(12) United States Patent
Giuffrida et al.

(10) Patent No.: US 9,314,190 B1
(45) Date of Patent: Apr. 19, 2016

(54) MOVEMENT DISORDER RECOVERY SYSTEM AND METHOD

(71) Applicants: Joseph P Giuffrida, Hinckley, OH (US); Dustin A Heldman, Shaker Heights, OH (US); Thomas O Mera, Westlake, OH (US)

(72) Inventors: Joseph P Giuffrida, Hinckley, OH (US); Dustin A Heldman, Shaker Heights, OH (US); Thomas O Mera, Westlake, OH (US)

(73) Assignee: Great Lakes NeuroTechnologies Inc., Cleveland, OH (US)

( * ) Notice: Subject to any disclaimer, the term of this patent is extended or adjusted under 35 U.S.C. 154(b) by 0 days.

(21) Appl. No.: 14/330,255

(22) Filed: Jul. 14, 2014

Related U.S. Application Data

(63) Continuation of application No. 13/185,287, filed on Jul. 18, 2011, now abandoned, which is a continuation-in-part of application No. 11/432,583, filed on May 11, 2006.

(51) Int. Cl.
*A61N 1/36* (2006.01)
*A61B 5/103* (2006.01)
*A61B 5/11* (2006.01)
*A61B 5/05* (2006.01)
*A61M 5/172* (2006.01)

(52) U.S. Cl.
CPC ... *A61B 5/11* (2013.01); *A61B 5/05* (2013.01); *A61M 5/1723* (2013.01); *A61N 1/36067* (2013.01)

(58) Field of Classification Search
CPC ........... A61N 1/36003; A61N 1/36067; A61N 1/36103; A61N 1/36128; A61N 1/36132
USPC ................................. 607/45, 48, 49
See application file for complete search history.

(56) References Cited

U.S. PATENT DOCUMENTS

| 6,066,163 | A  * | 5/2000 | John .............................. 607/45 |
| 7,324,851 | B1 * | 1/2008 | DiLorenzo ...................... 607/45 |
| 2005/0234309 | A1 * | 10/2005 | Klapper ......................... 600/300 |
| 2006/0173510 | A1 * | 8/2006 | Besio et al. ..................... 607/45 |

* cited by examiner

*Primary Examiner* — Allen Porter, Jr.
(74) *Attorney, Agent, or Firm* — Brian Kolkowski

(57) ABSTRACT

Most particularly, the present invention relates to a customized and adaptive movement recovery system and a method of improving the functional motor recovery of a subject with a movement disorder. The present invention provides for a system and method, which in some embodiments can accurately quantify treatment device parameters and protocols including electrical stimulation amplitude (volts/amps), frequency (Hz), and pulse width (microseconds), and medication titrations, doses, and times by utilizing accelerometric, gyroscopic or other movement related information, such as electromyography (EMG) data, or the like, and a central database, or system of databases, of patient and treatment histories. In other embodiments, the system and method provide for an adaptive central database system and automated control of movement disorder treatment devices.

10 Claims, 20 Drawing Sheets

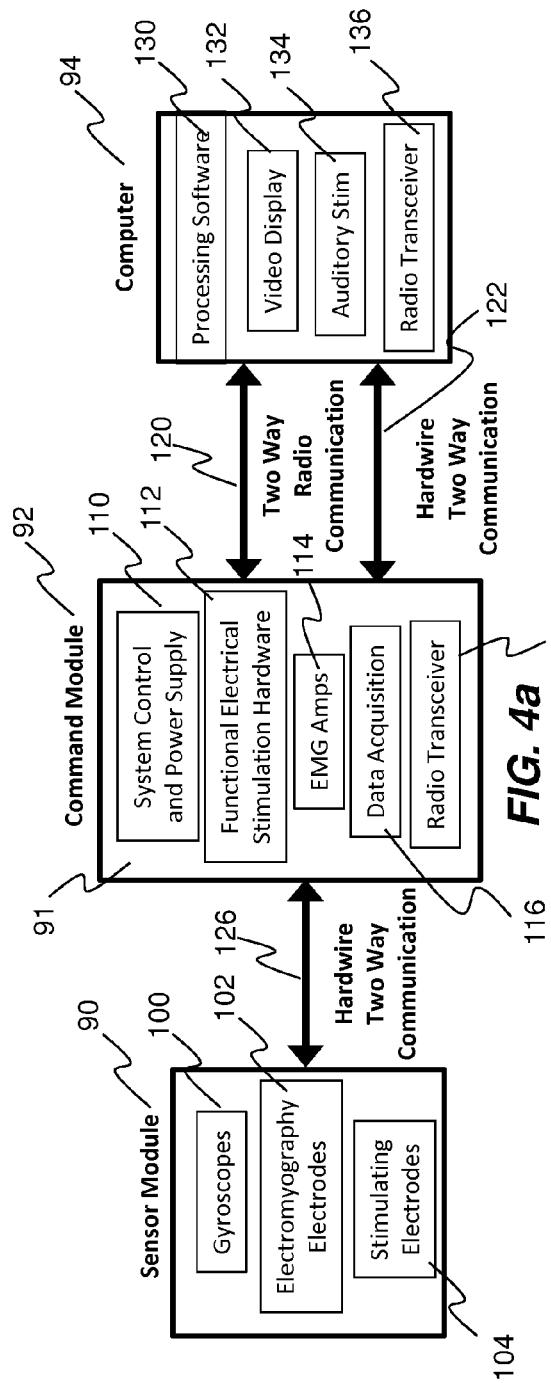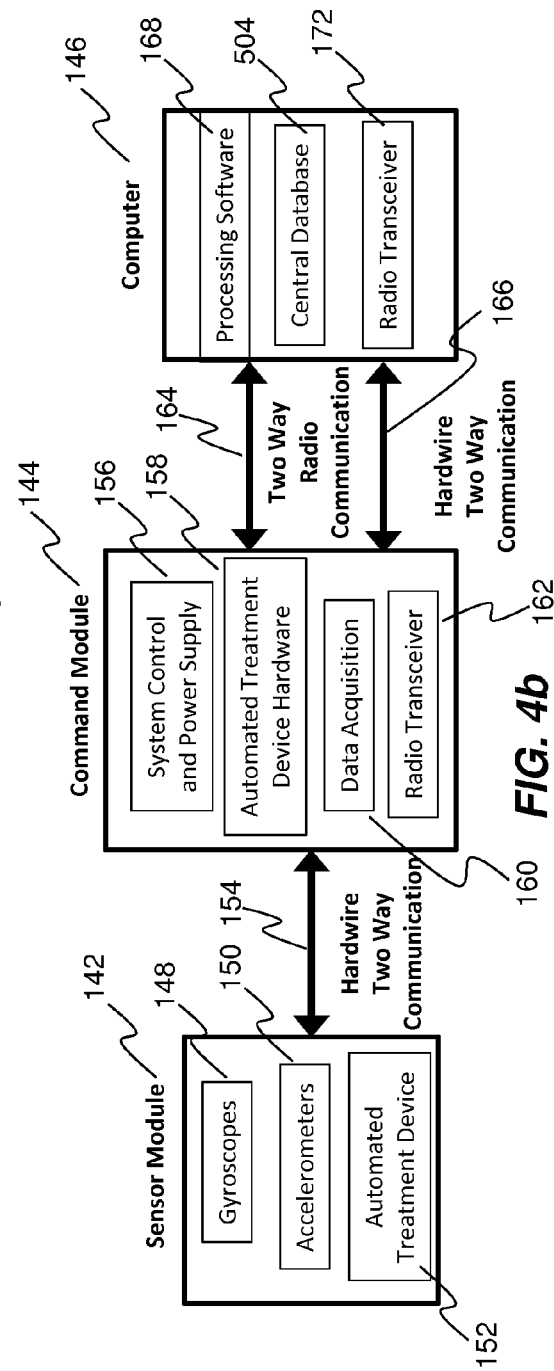

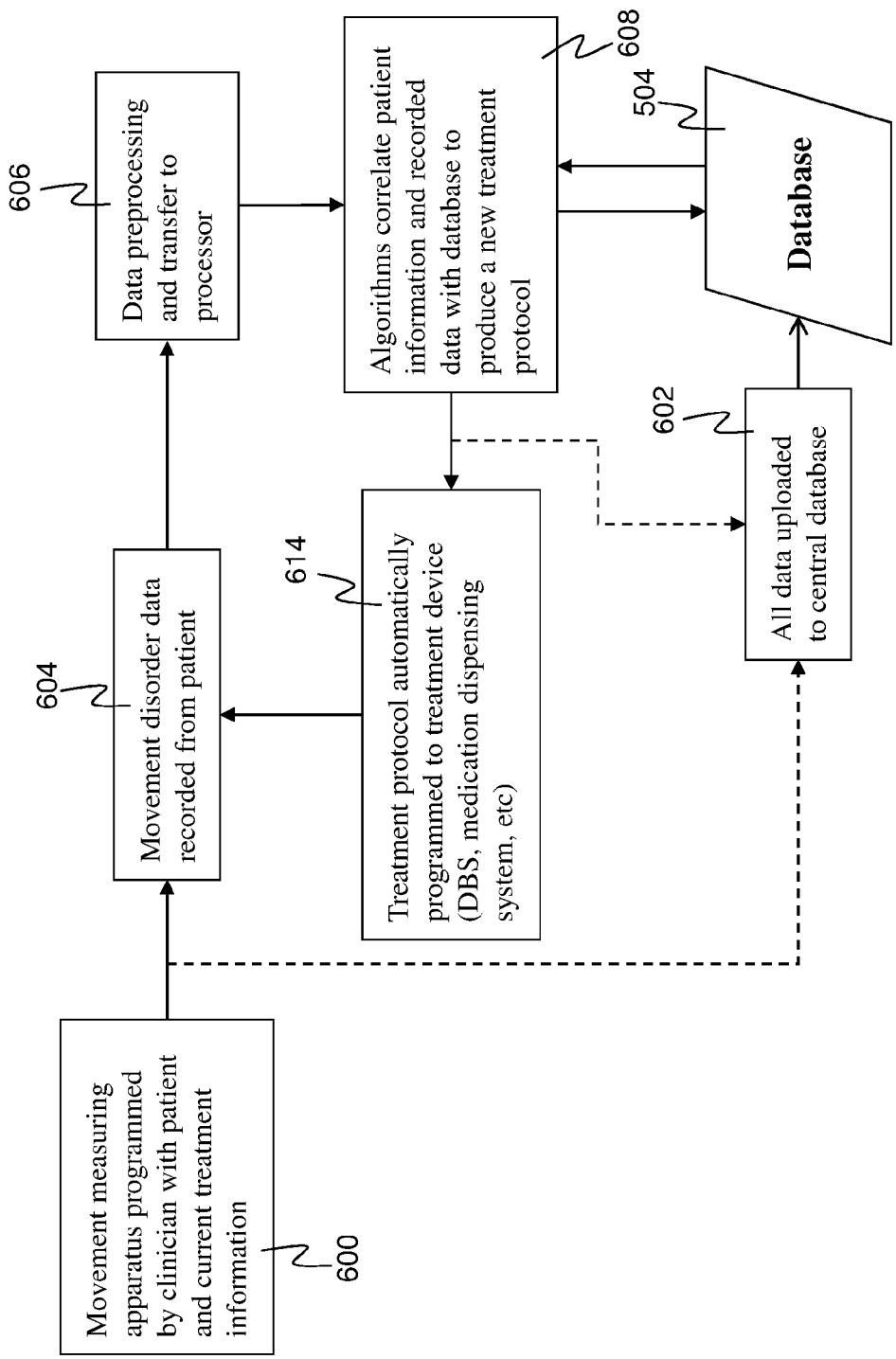

MOVEMENT DISORDER RECOVERY SYSTEM AND METHOD

CROSS-REFERENCE TO RELATED APPLICATIONS

This application is a continuation of U.S. patent application Ser. No. 13/185,287, which was filed on Jul. 18, 2011, and which was a continuation-in-part U.S. patent application Ser. No. 11/432,583, which was filed on May 11, 2006.

STATEMENT REGARDING FEDERALLY-SPONSORED RESEARCH OR DEVELOPMENT

The U.S. Government has a paid-up license in this invention and the right in limited circumstances to require the patent owner to license others on reasonable terms provided for by the terms of grant numbers 2R44NS043816-02, 1R43NS046976-01A1, 1R43NS053032-01, 1R43NS055428-01 from the National Institutes of Health, National Institute of Neurological Disorders and Stroke.

BACKGROUND OF THE INVENTION

1. Field of the Invention

The present invention relates to a system and method for monitoring symptoms of movement disorders. More particularly, the present invention relates to such a system and method for monitoring symptoms of movement disorders and also a system for providing possible treatment methods for those symptoms. The present invention further relates to a method and system of providing possible treatment methods for movement disorder symptoms based on a correlation of the particular subject's movement data to a database of similar data. Most particularly, the present invention relates to a patient customized and adaptive movement recovery system, and method of improving the functional motor recovery of a subject with a movement disorder.

2. Technology Review

Movement disorders resulting from brain or spinal cord injury, or abnormalities affect millions of individuals worldwide. These movement disorders can be the result of stroke, cerebral palsy (CP), Parkinson's disease (PD) and the like. Since these injuries or abnormalities can affect most parts of the brain or the spinal cord, the possible results are numerous. Effects can include motor paralysis, sensory disturbances, language difficulties, memory problems, tremor, and issues with swallowing or slurred speech. These disorders can also result in loss of motor control of the individual's extremities, including paralysis or weakness, abnormal muscle tone, abnormal posture, abnormal movement synergies and loss of coordination. Many individuals that experience a movement disorder develop a physical disability that affects activities of daily living including eating, dressing and personal hygiene.

Two of the most prevalent treatment methods currently implemented for alleviating movement disorder symptoms are electrical stimulation, particularly deep brain stimulation (DBS) and functional electrical stimulation (FES), and the use of pharmaceutical treatments (i.e., medications, drugs). The effectiveness of both electrical stimulation and pharmaceutical treatment vary widely depending on a patient's individual symptoms and the causes thereof. Furthermore, the efficacy of each treatment method generally varies greatly throughout the day, as well as the life of the treatment due to numerous environmental and circumstantial factors that play a role in the onset of such symptoms.

Additional treatments may include surgery and physiotherapy which are used to help counter the effects of movement disorders. Little evidence, however, exists of their efficacy. Optionally, occupational and physical therapy contribute to the functional recovery of patients suffering from movement disorders. Research has shown that forced use through repetitive motor activity may provide the basis for motor learning and functional recovery. For example repetitive movement execution or repetitive sensorimotor training may be of great benefit for functional outcomes of motor rehabilitation of the arm and hand. Physical therapy has been found to lead to enhancement of motor function if the individual performs voluntary motor activities with that arm. Methods used by rehabilitation therapists to effectively stimulate functional plasticity and motor recovery include active/passive range of motion, bilateral training, forced use, and constraint induced therapy.

Both simple, isolated, single joint movements and complex movement tasks improve motor recovery. Repetitive training of complex movements has been found to provide significant improvement of motor function in distal and proximal affected upper extremities. Grip strength, another important requirement for daily living, is also significantly improved. The repetitive execution of complex motor movements accelerates and supports functional recovery. Increasing the amount of time spent as well as using behavioral methods to encourage motor learning helps improve function for those individuals suffering from a movement disorder.

Deep brain stimulation (DBS) and functional electrical stimulation (FES) are two forms of electrical stimulation that have been used by clinicians to help counter the effects of certain movement disorders. For example, DBS is the stimulation of target areas of the central nervous system to effect therapeutic benefit. Such stimulation has been accomplished with, for example, implanted electrodes that deliver electrical stimulation to target brain regions. Although the exact neurological mechanisms by which DBS therapies succeed are complex and are not yet fully understood, such therapies have proven effective in treating Parkinson's disease motor symptoms (such as tremor, bradykinesia, rigidity, and gait/balance disturbances), and investigation into the use of DBS for the treatment of this and other neurological and mental health disorders, including major depression, obsessive-compulsive disorder, tinnitus, obesity, criminal tendencies, and antisocial disorders, is ongoing.

Functional electrical stimulation (FES) has been found to be advantageous for individuals suffering from CP partially because it is non-invasive and causes minimal side effects. FES stimulates the muscles to create a contraction. Some individuals with CP have paralyzed muscles while others with early acquired motor deficits can have difficulty producing selective movements in an affected extremity due to a form of apraxia caused by defective motor planning in early infancy. Therefore, a muscle normally required for a task, but inactive due to CP could potentially be included during therapy using functional electrical stimulation. Additionally, utilizing functional electrical stimulation at the sensory level helps the individual to localize the muscle they are trying to use for a particular task.

During electrical stimulation, electrical pulses characterized by amplitude (volts/amps), frequency (Hz), and pulse width (microseconds) are regulated by a pulse generator placed beneath the skin on the chest or worn externally. The pulse generator typically includes a battery and circuitry for telemetered communication with an external programming device used to adjust, or "tune," lead stimulation parameters, which may include stimulation frequency, amplitude, pulse width (or wavelength), and contact configuration (that is, the selection of which electrodes are utilized from among the electrodes available on a lead, and, if two or more electrodes are active, the relative polarity of each). These parameters are initially set during implantation surgery and are then further fined-tuned in the outpatient clinic or in a doctor's office following surgery to maximize therapeutic benefit and minimize undesirable stimulation-induced side effects.

While various pharmaceutical agents exist for treatment of movement disorder symptoms, oral administration of L-3,4-dihydroxyphenylalanine ("levodopa" or "L-DOPA") is presently the most common, particularly for PD, and will thus be the focus of the examples set forth herein. Levodopa is a dopamine precursor molecule that alleviates symptoms by crossing the blood brain barrier and being subsequently converted into dopamine. During treatment, levodopa is typically taken orally by a subject several times per day at intervals specified by a physician. The dosage, taken at such intervals, allows the level of levodopa in the blood to remain somewhat constant throughout the day. However, physiological differences between subjects means that there will be no single dosage of levodopa that will be effective for all subjects. It will be appreciated that this same effect is also observed in pharmaceutical treatment of subjects with various other movement disorders besides PD.

This lack of uniformity among subjects and the temporal variation of levodopa efficacy in treating PD raise a need for a method and/or device that allows a physician to more optimally customize a subject's drug regimen based on the drug's effect on a specific subject at specific times and under a subject's specific circumstances. Automated medication titration and delivery systems can help physician's achieve some of these goals, however, the current technology is subject to a number of problems, for example, the devices cannot be controlled in real-time to account for a patient's dyskinesias and are limited to a single medication.

While electrical stimulation and pharmaceutical treatments can improve functional outcomes for patients with movement disorders, these treatments can require frequent returns and long stays in a treatment center. What is needed is a system and/or method that allows individuals to customize their therapy outside a treatment center. What is also needed is a system and/or method that allows individuals to continue and improve treatment without the need for a clinician to be available to apply the treatment. What is still further needed is a system and/or method that allows for intensive home treatment of individuals affected with movement disorders.

It is therefore an object of the present invention to provide a system and method for treating individuals with movement disorders without needing a clinician to apply the treatment. It is still another object of the present invention to provide a system, which provides functional recovery. It is still another object of the present invention to provide a system and method that provides feedback and recommendations to the clinician providing a patient with customized and adaptive treatment. It is still further another object of the present invention to provide a portable system which the individual can carry with themselves so they might be treated at home, on vacation or while away from home on business. Finally it is the object of the present invention to provide a system and method for movement disorder recovery that can be remotely accessed by the clinician.

SUMMARY OF THE INVENTION

The present invention relates to a system and method for monitoring symptoms of movement disorders. More particularly, the present invention relates to such a system and method for monitoring symptoms of movement disorders and also a system for providing possible treatment methods including titrations, changes and recommendations for those symptoms. The present invention further relates to a system and method of providing possible treatment methods for movement disorder symptoms based on a correlation of the particular subject's movement data with a database of similar data. Most particularly, the present invention relates to a patient customized and adaptive movement recovery system and method of improving the functional motor recovery of a subject with a movement disorder. The present invention provides for a system and method, that can determine patient customized electrical stimulation parameters such as amplitude, current, frequency, pulse width, and activation timing by utilizing accelerometric, gyroscopic or other movement related information, such as electromyography (EMG) data, or the like, and a central database, or system of databases, of patient and treatment histories. In other instances, the system and method provide for pharmaceutical parameters such as drug titrations, doses and times. Optionally, the present invention includes but is not limited to compliance, task time spent, muscle coordination and functional improvement by utilizing kinetic, gyroscopic or other movement related information, and/or electromyography (EMG) data. In other instances, the system and method provide for functional electrical stimulation (FES) to help control the exercise therapy. The present invention further includes a system and methods of storing and cataloging the movement related information and patient specific treatments in a central database system to be used for continuous improvement of the treatment protocols for use with subjects in the future.

The system and method of the present invention may provide a small, lightweight, untethered, easy to don system for home treatment of movement disorder subjects. In other instances, the system or method may optionally allow for greater flexibility by allowing for an intense therapy program at home around a subject's schedule. In even other instances, the system or method may provide clinicians access to recommended treatment protocols during tuning sessions with movement disorder subjects. In even other instances, the system or method may encourage a subject to use a paretic limb with a unique interface and real-time feedback. In still other instances, the system or method may improve therapy for the underprivileged or those living in remote locations where access to such clinician treatment is limited. In still even other instances, the system or method may provide a unique research tool to further quantify the effects of new novel treatments. In still another instance, the system or method allows a physician, clinician or technician to review and modify therapy from an external location such as transmitting reports from a subject's home to a physician's office via the internet so that therapy may be monitored and/or modified on or off line. In still another instance, central patient information and recorded movement databases are used together to customize treatment protocols.

A number of embodiments of the present invention are envisioned in this disclosure. These embodiments are examples of the many embodiments encompassed by the present invention, but do not in any way limit the many other embodiments covered by this disclosure.

In one embodiment, the present invention includes a portable therapy system for rehabilitation of a subject's movement disorder comprising a sensor for measuring a subject's electrical muscle activity having a signal related to the subject's electrical muscle activity and a device for providing a stimulus to the subject to respond to wherein the subject's ability to respond to the stimulus is calculated based in part on the signal for measuring the subject's electrical muscle activity.

In another embodiment, the present invention includes a portable therapy system for rehabilitation of a subject's movement disorder comprising a device for measuring a subject's arm or leg motion comprising at least one motion sensor having a signal for measuring; and a device for providing a stimulus or instructions to the subject to respond to by movement of an arm or a leg being measured wherein the device for measuring a subject's arm or leg motion does not substantially limit the subject's arm or leg motion and the ability to respond to the stimulus or instructions is calculated based in part on the signal for measuring the subject's arm or leg motion.

In still another embodiment, the present invention includes a portable therapy system for rehabilitation of a subject's movement disorder comprising a first sensor for measuring a subject's external body motion having a signal related to the subject's external body motion; a second sensor for measuring a subject's electrical muscle activity having a signal related to the subject's electrical muscle activity; and a device for providing a stimulus or instructions to the subject to respond to wherein the subject's ability to respond to the stimulus or instructions is calculated based in part on the signals of the first and second sensors.

In still another embodiment, the present invention includes a portable therapy system for rehabilitation of a subject's movement disorder comprising a sensor for measuring a subject's electrical muscle activity having a signal related to the subject's electrical muscle activity; a first device providing video and/or audio outputs for providing a task for the subject to perform; and a second device for providing functional electrical stimulation to the subject; wherein the subject's ability to complete the task is estimated or calculated based in part on the signal for measuring the subject's electrical muscle activity and the second device can be activated in order to assist the subject in completing the task based in part on the estimation or calculation of the subject's ability to complete the task.

In still another embodiment, the present invention includes a portable therapy system for rehabilitation of a subject's movement disorder comprising a first device for measuring a subject's arm or leg motion comprising at least one motion sensor having a signal for measuring; a second device for providing video and/or audio outputs for providing a task for the subject to perform; and a third device for providing functional electrical stimulation to the subject; wherein the subject's ability to complete the task is estimated or calculated based in part on the signal for measuring the motions of the subject's arm and/or leg and the third device can be activated in order to assist the subject in completing the task based in part on the estimation or calculation of the subject's ability to complete the task.

In still another embodiment, the present invention includes a portable therapy system for rehabilitation of a subject's movement disorder comprising a sensor for measuring a subject's electrical muscle activity having a signal related to the subject's electrical muscle activity; a sensor for measuring the subject's body motion having a signal related to the subject's body motion; a first device providing video and/or audio outputs for providing a task for the subject to perform; and a second device for providing functional electrical stimulation to the subject; wherein the subject's ability to complete the task is estimated or calculated based in part both on the signal for measuring the subject's electrical muscle activity and the signal related to the subject's body motion, and the second device can be activated in order to assist the subject in completing the task based in part on the estimation or calculation of the subject's ability to complete the task.

In still another embodiment, the present invention includes a method of rehabilitating a subject having a movement disorder comprising the steps of showing a subject a video; performance of a task involving leg and/or arm motion by the subject in response to the video; measuring the subject's leg and/or arm motion in response to the video with a sensor with an output signal; and calculating with a processor the subject's ability complete the task based in part on the signal from the sensor.

In still another embodiment, the present invention includes a method of rehabilitating a subject having a movement disorder comprising the steps of showing a subject having legs and/or arms a video; performance of a task involving leg and/or arm motion by the subject in response to the video; measuring the subject's leg and/or arm motion in response to the video with a sensor having an output signal; determining with a processor whether the subject's was able to complete the task based in part on the output signal from the sensor; and if not or if only partially completed, applying functional electrical stimulation to at least one of the subject's legs and/or arms to assist the subject in completing the task.

In still another embodiment, the present invention includes a method of rehabilitating a subject having a movement disorder comprising the steps of placing at least one EMG sensor on a subject's leg and/or arm; showing the subject a video; performance of a task involving a leg and/or arm motion by the subject in response to the video; measuring the subject's leg and/or arm muscle activity in response to the video with the at least one EMG sensor with an output signal placed on the subject's leg and/or arm; and calculating with a processor the subject's ability to complete the task based in part on the output signal from the at least one EMG sensor.

In still another embodiment, the present invention includes a method of rehabilitating a subject having a movement disorder comprising the steps of placing at least one motion sensor on a subject's leg and/or arm; showing the subject a video; performance of a task involving a leg and/or arm motion by the subject in response to the video; measuring the subject's leg and/or arm motion in response to the video with the at least one motion sensor with an output signal placed on the subject's leg and/or arm; and calculating with a processor the subject's ability to complete the task based in part on the output signal from the at least one motion sensor.

In still another embodiment, the present invention includes a method of rehabilitating a subject having a movement disorder comprising the steps of placing at least one motion sensor and at least one EMG sensor on a subject's leg and/or arm; showing the subject a video; performance of a task involving a leg and/or arm motion by the subject in response to the video; measuring the subject's leg and/or arm muscle activity in response to the video with the at least one EMG sensor with a first output signal placed on the subject's leg and/or arm; measuring the subject's leg and/or arm motion in response to the video with the at least one motion sensor with a second output signal placed on the subject's leg and/or arm; and calculating with a processor the subject's ability to complete the task based in part on both on the first output signal from the at least one EMG sensor and the second output signal from the at least one motion sensor.

In still another embodiment, the present invention includes a system for providing treatment recommendations for movement disorders comprising a movement measuring apparatus for acquiring movement data corresponding to movement of a subject comprising at least one sensor and a transmitter; an algorithm for correlating the movement data acquired from the subject with movement data stored in at least one central database; at least one central database where historical movement data is stored; a processor for correlating the movement data to at least one central database and determining a recommended treatment using the algorithm; and a device for outputting or otherwise communicating the recommended treatment to a clinician or other user for review and administering.

In still another embodiment, the present invention includes a system for providing treatment for movement disorders comprising a movement measuring apparatus for acquiring movement data corresponding to movement of a subject comprising at least one sensor and a transmitter; an algorithm for correlating the movement data acquired from the subject with movement data stored in at least one central database; at least one central database where historical movement data is stored; a processor for correlating the movement data to at least one central database and determining a customized treatment using an algorithm; and a medical delivery device for automatically administering the customized treatment to the subject.

In still another embodiment, the present invention includes a method for providing treatment recommendations for movement disorders comprising steps of providing a movement measuring apparatus comprising at least one sensor and a transmitter; acquiring movement data from a subject wearing the movement measuring apparatus, the movement data corresponding to movement of the subject; transmitting the movement data from the movement measuring apparatus to a processor; training an algorithm to correlate acquired movement data with at least one database of movement data; correlating with the processor the subject's movement data to at least one central database comprising movement data from a plurality of other subjects using the algorithm; and determining a recommended treatment based at least in part on the correlation between the subject's movement data and the at least one central database.

In still another embodiment the present invention includes a method for providing treatment recommendations for movement disorders comprising steps of providing a movement measuring apparatus comprising at least one sensor and a transmitter; acquiring movement data from a subject wearing the movement measuring apparatus, the movement data corresponding to movement of the subject; transmitting the movement data from the movement measuring apparatus to a processor; training an algorithm to correlate acquired movement data with at least one database of movement data; correlating with the processor the subject's movement data to at least one central database comprising movement data from a plurality of other subjects using the algorithm; determining a recommended treatment based at least in part on the correlation between the subject's movement data and the at least one central database; and outputting the recommended treatment to a clinician or other user for review and implementation.

In still another embodiment, the present invention includes a method for providing treatment for movement disorders comprising steps of providing a movement measuring apparatus comprising at least one sensor and a transmitter; acquiring movement data from a subject wearing the movement measuring apparatus, the movement data corresponding to movement of the subject; transmitting the movement data from the movement measuring apparatus to a processor; training an algorithm to correlate acquired movement data with at least one database of movement data; correlating with the processor the subject's movement data to at least one central database comprising movement data from a plurality of other subjects using the algorithm; determining a customized treatment based at least in part on the correlation between the subject's movement data and the at least one central database; and outputting the customized treatment to a medical delivery device for administering the determined treatment.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

BRIEF DESCRIPTION OF THE DRAWINGS

FIG. 4. Block diagram of two embodiments of the movement disorder recovery system for a) report systems; and b) automated treatment systems.

DESCRIPTION OF THE PREFERRED EMBODIMENT

Figure 1A:
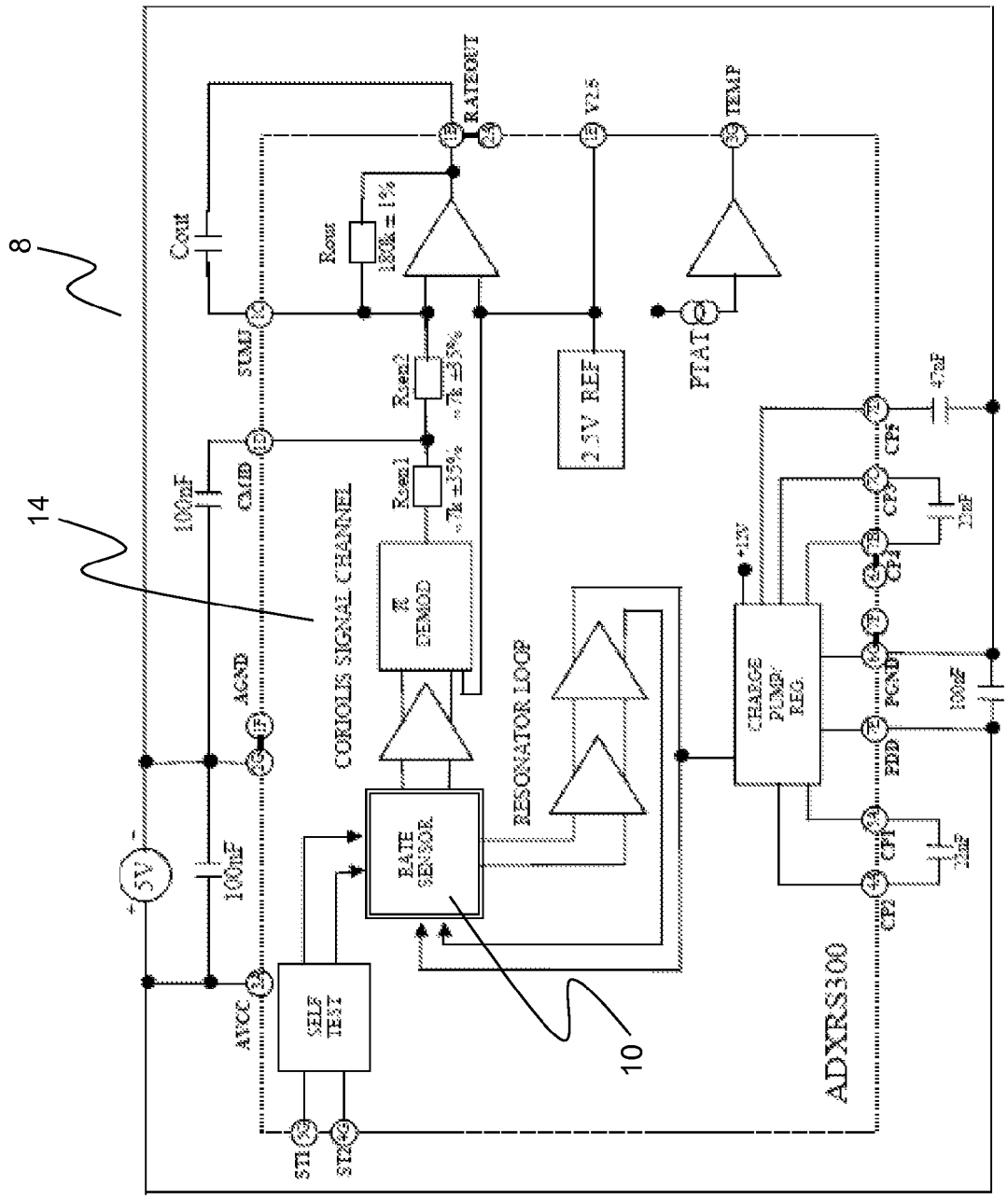
FIG. 1. Electrical schematics of gyroscopes useful in the present invention: a) and b) are schematics of single-axis gyroscopes; and c) dual-axis gyroscope.

The present invention relates to a patient customized and adaptive movement recovery system and method of improving the functional motor recovery of a subject with a movement disorder. The devices, systems and methods of the various embodiments of the present invention are used for customizing and monitoring treatment for various types of movement disorders. Allowing patients to receive customized treatment in a non-hospital setting such as their home increases treatment efficacy and hence the amount of functional improvement. Movement disorders and their symptoms for purposes of this application include, but are not limited to, those movement disorders stemming from a disease or injury to the nervous system where electrical stimulation, pharmaceutical treatment, or physical therapy has been or are determined to benefit the subject by either improving the subject's movement or by preventing either further degradation or not as rapid degradation of the subject's condition. Examples of such movement disorders and their symptoms that can be treated with the systems and methods of the present invention include, but are not limited to, stroke, cerebral palsy, Parkinson's disease (PD), essential tremor, dystonia, and Tourette's syndrome, such as tremor, bradykinesia, rigidity, gait/balance disturbances, and dyskinesia. The subject on which the devices, system or method is used is a human or other form of animal.

The devices worn by the various subjects or the different systems of the various embodiments of the present invention are preferably portable. By portable it is meant among other things that the device is capable of being transported relatively easily. Relative easy in transport means that the therapy device is easily worn and carried, generally, in a carrying case to the point of use or application and then worn by the subject without significantly affecting their range of motion. Furthermore the portable therapy device preferably should be relatively light-weight. By relatively light-weight, preferably the device weighs less than about 3 lbs., more preferably less than about 2 lbs., even more preferably less than about 1 lb., even more preferably less than about 0.5 lbs., still more preferably less than about 0.1 lbs., and most preferably less than about 20 grams. By being light-weight and further compact, the therapy device should gain greater acceptance for use by the subject. The entire therapy system including the therapy device, feedback modality, and other components including any processors, computers, video screens and the like preferably weigh less in total than about 15 lbs., more preferably less than about 10 lbs., even more preferably less than about 5 lbs., still more preferably less than about 2 lbs., and most preferably less than about 0.5 lbs. This system more preferably can fit in a reasonably sized carrying case so the patient or their caregiver can easily transport the system.

The devices of the various embodiments of the present invention can form part of a system for use by a physician, veterinarian, technician or clinician for treatment and further diagnosis of a subject's movement disorder; for pharmaceutical research; or for delivery of pharmaceutical compounds. Other elements of this system may include but are not limited to receivers, routers, communication devices, processors, displays, drug delivery devices, electrical stimulators, databases, algorithms, and the like, some of which are described further in various embodiments described in more detail below.

Various embodiments of the present invention may include different sensors known to those skilled in the art to sense motion, physiological conditions of the subject and the like. Of these various embodiments of the present invention some may include a sensor for measuring a subject's external body motion. Many types of sensors are known by those skilled in the art for measuring external body motion. These sensors include but are not limited to accelerometers, gyroscopes, magnetometers, resistive bend sensors, load cells, combinations thereof, and the like. The part of the body wearing the sensor and being measured for motion may be a limb (as at a wrist, ankle, heel, thigh, or finger) or may be the trunk of the body (as at a shoulder, waist, or torso) or according to other techniques known to those skilled in the art. In most embodiments, a combination using at least three axes each of an accelerometer and gyroscope is preferably used at a combination of limb and trunk locations.

Figure 1B:
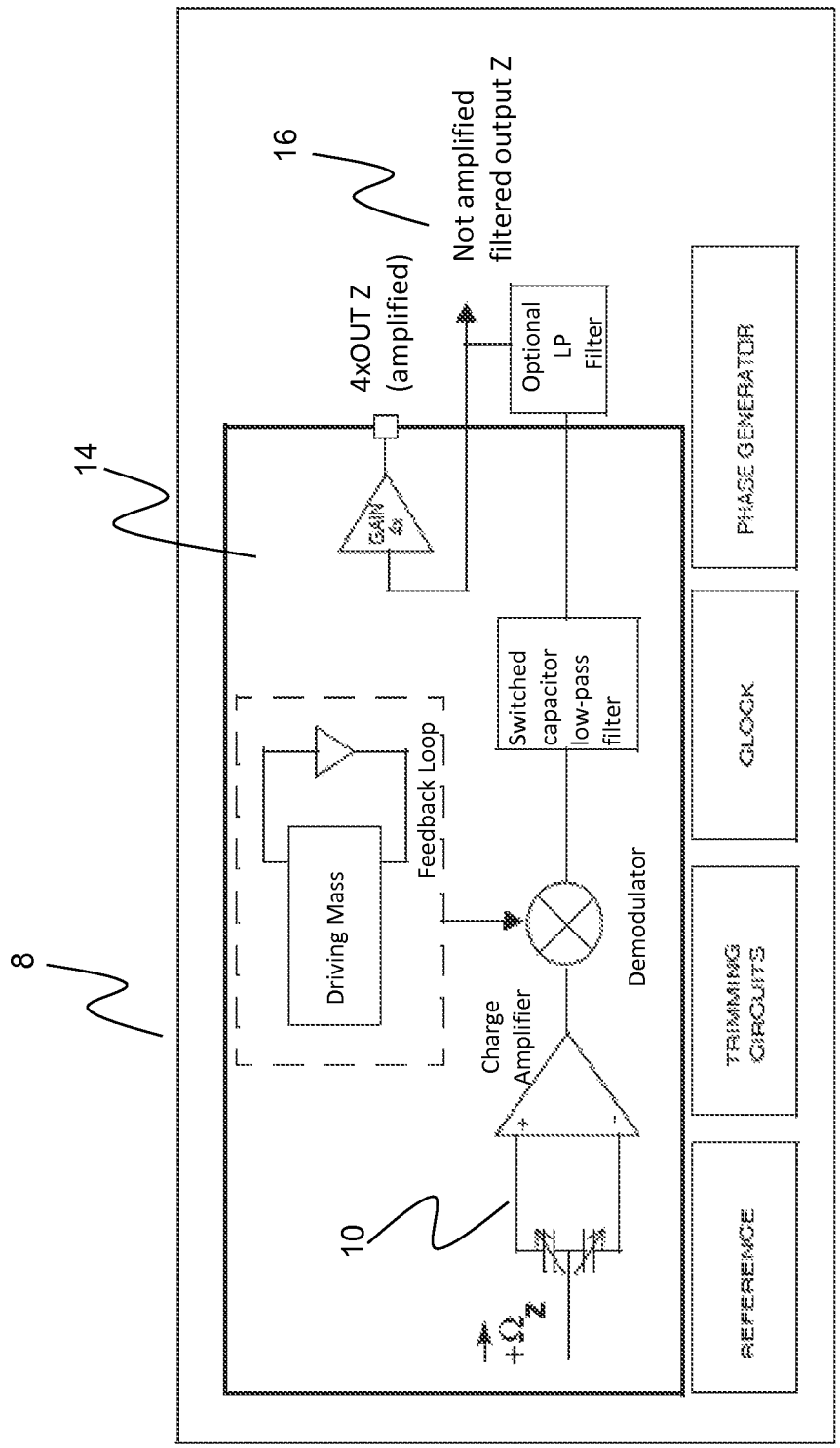
Figure 1C:
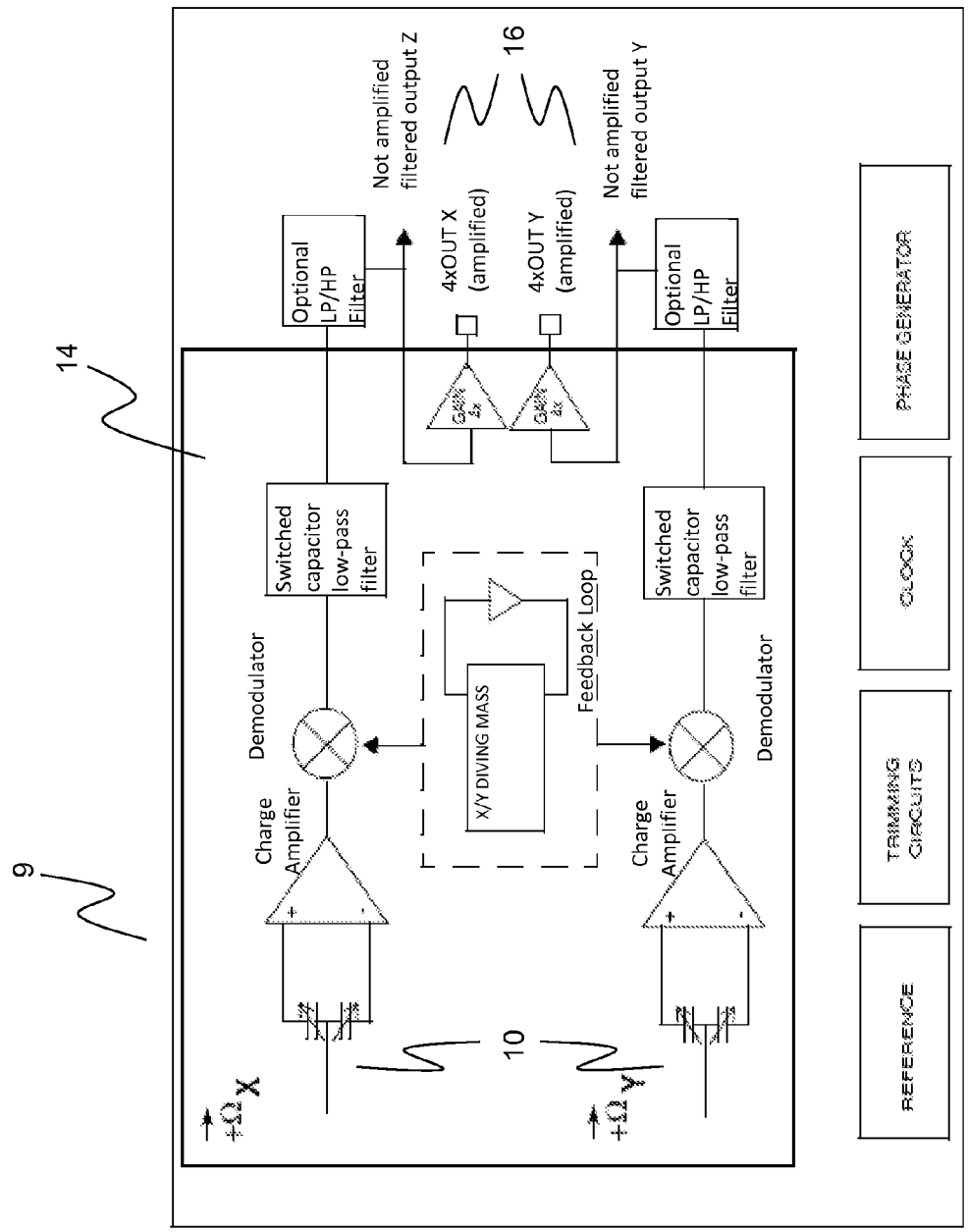

FIGS. 1a and 1b are electrical schematic diagrams for two embodiments of a single axis gyroscope 8 used as a sensor or in a sensor of the present invention. The sensor element 10 functions on the principle of the Coriolis Effect and a capacitive-based sensing system. Rotation of the sensor 10 causes a shift in response of an oscillating silicon structure resulting in a change in capacitance. An application specific integrated circuit (ASIC) 14, using a standard complimentary metal oxide semiconductor (CMOS) manufacturing process, detects and transforms changes in capacitance into an analog output voltage 16, which is proportional to angular rate. The sensor element design utilizes differential capacitors and symmetry to significantly reduce errors from acceleration and off-axis rotations. FIG. 1c is an electrical schematic for one embodiment of a dual axis gyroscope 9 also based on the Coriolis Effect as described for FIGS. 1a and 1b. The preferred three axis combination can be achieved by any combination and orientation of three single-axis sensors, a single-axis and dual-axis sensor, a single three-axis sensor (not shown as a gyroscope), two dual-axis sensors whereby the repeated axis is averaged, or other combinations and orientations known to those skilled in the art to produce yaw, pitch, and roll measurements.

Figure 2A:
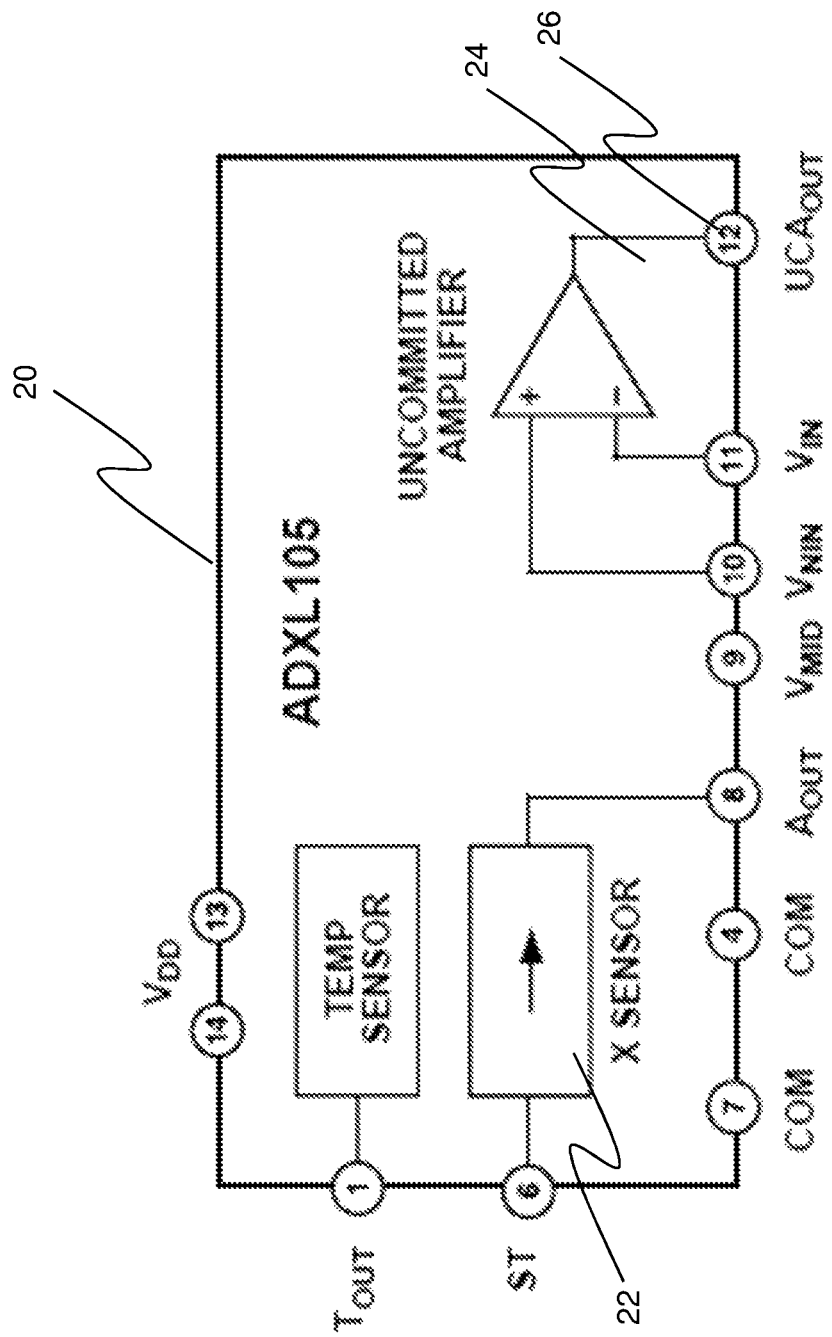
FIG. 2. Electrical schematics accelerometers useful in the present invention: a) single-axis accelerometer; b) dual-axis accelerometer and c) three-axis accelerometer.

FIG. 2a is an electrical schematic diagram for one embodiment of a single axis accelerometer of the present invention. The accelerometer 20 is fabricated using a surface micro-machining process. The fabrication technique uses standard integrated circuit manufacturing methods enabling all signal processing circuitry to be combined on the same chip with the sensor 22. The surface micro-machined sensor element 22 is made by depositing polysilicon on a sacrificial oxide layer that is then etched away leaving a suspended sensor element. A differential capacitor sensor is composed of fixed plates and moving plates attached to the beam that moves in response to acceleration. Movement of the beam changes the differential capacitance, which is measured by the on chip circuitry. All the circuitry 24 needed to drive the sensor and convert the capacitance change to voltage is incorporated on the chip requiring no external components except for standard power supply decoupling. Both sensitivity and the zero-g value are ratiometric to the supply voltage, so that ratiometric devices following the accelerometer (such as an analog to digital converter (ADC), etc.) will track the accelerometer if the supply voltage changes. The output voltage (VOUT) 26 is a function of both the acceleration input and the power supply voltage (VS).

Figure 2B:
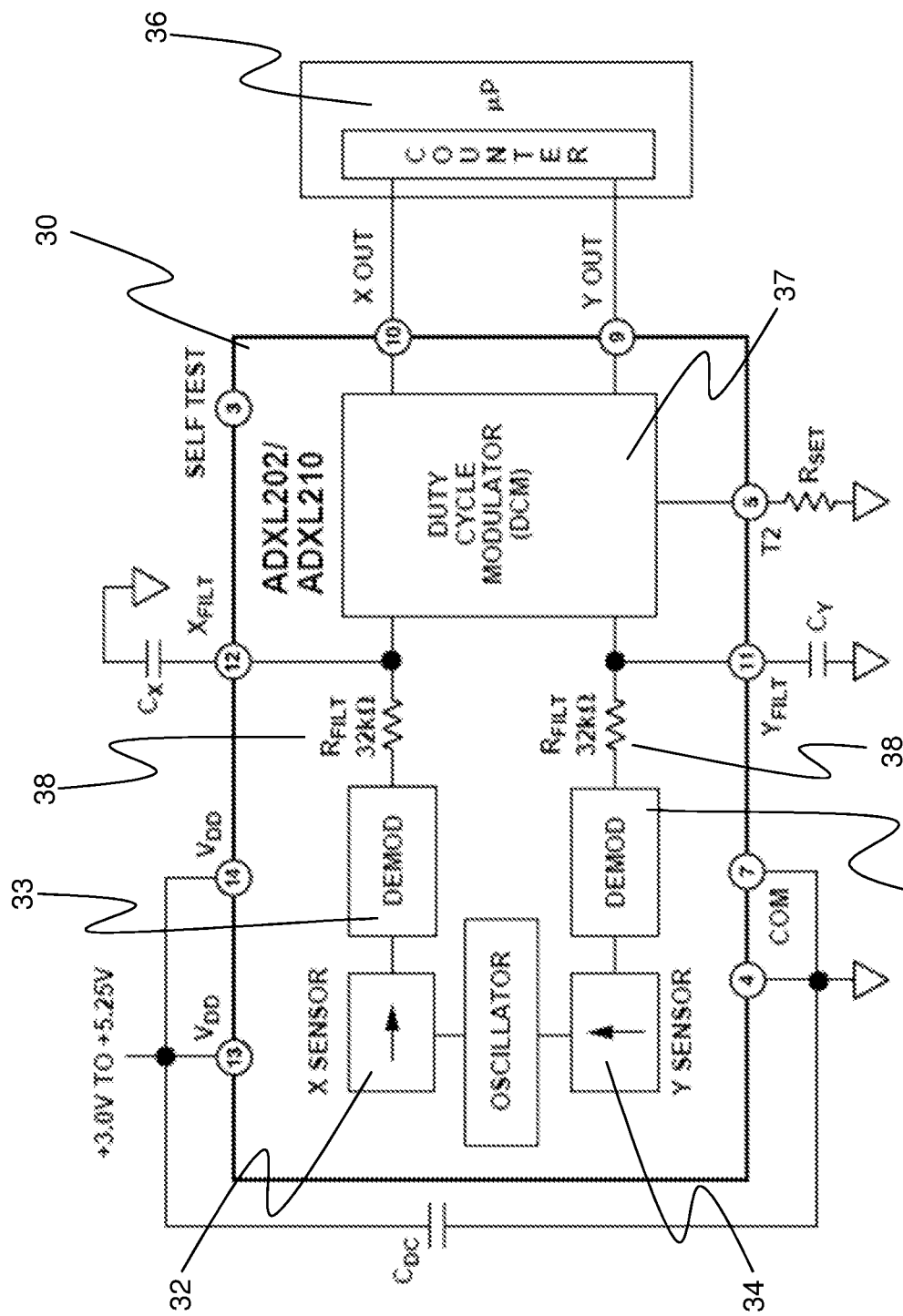

FIG. 2b is an electrical schematic diagram for one embodiment of a dual axis accelerometer of the present invention. The dual axis acceleration measurement system 30 is on a single monolithic IC. They contain a polysilicon surface-micromachined sensor and signal conditioning circuitry to implement an open-loop acceleration measurement architecture. For each axis 32, 34 an output circuit converts the analog signal to a duty cycle modulated (DCM) digital signal that can be decoded with a counter/timer port 36 on a microprocessor. The dual axis accelerometer is capable of measuring both positive and negative accelerations. The sensor 30 is a surface micromachined polysilicon structure built on top of the silicon wafer. Polysilicon springs suspend the structure over the surface of the wafer and provide a resistance against acceleration forces. Deflection of the structure is measured using a differential capacitor that consists of independent fixed plates and central plates attached to the moving mass. The fixed plates are driven by 180-degree ☐out of phase square waves. Acceleration will deflect the beam and unbalance the differential capacitor, resulting in an output square wave whose amplitude is proportional to acceleration. Phase sensitive demodulation techniques are then used to rectify the signal and determine the direction of the acceleration. The output of the demodulator 33, 35 drives a duty cycle modulator (DCM) 37 stage through a 32 kOhm ☐resistor 38. At this point a pin is available on each channel to allow the user to set the signal bandwidth of the device by adding a capacitor. This filtering improves measurement resolution and helps prevent aliasing. After being low-pass filtered, the analog signal is converted to a duty cycle modulated signal by the DCM stage 37. A single resistor sets the period for a complete cycle (T2). A 0 g acceleration produces a nominally 50% duty cycle. The acceleration signal can be determined by measuring the length of the T1 and T2 pulses with a counter/timer or with a polling loop using a low cost microcontroller.

Figure 2C:
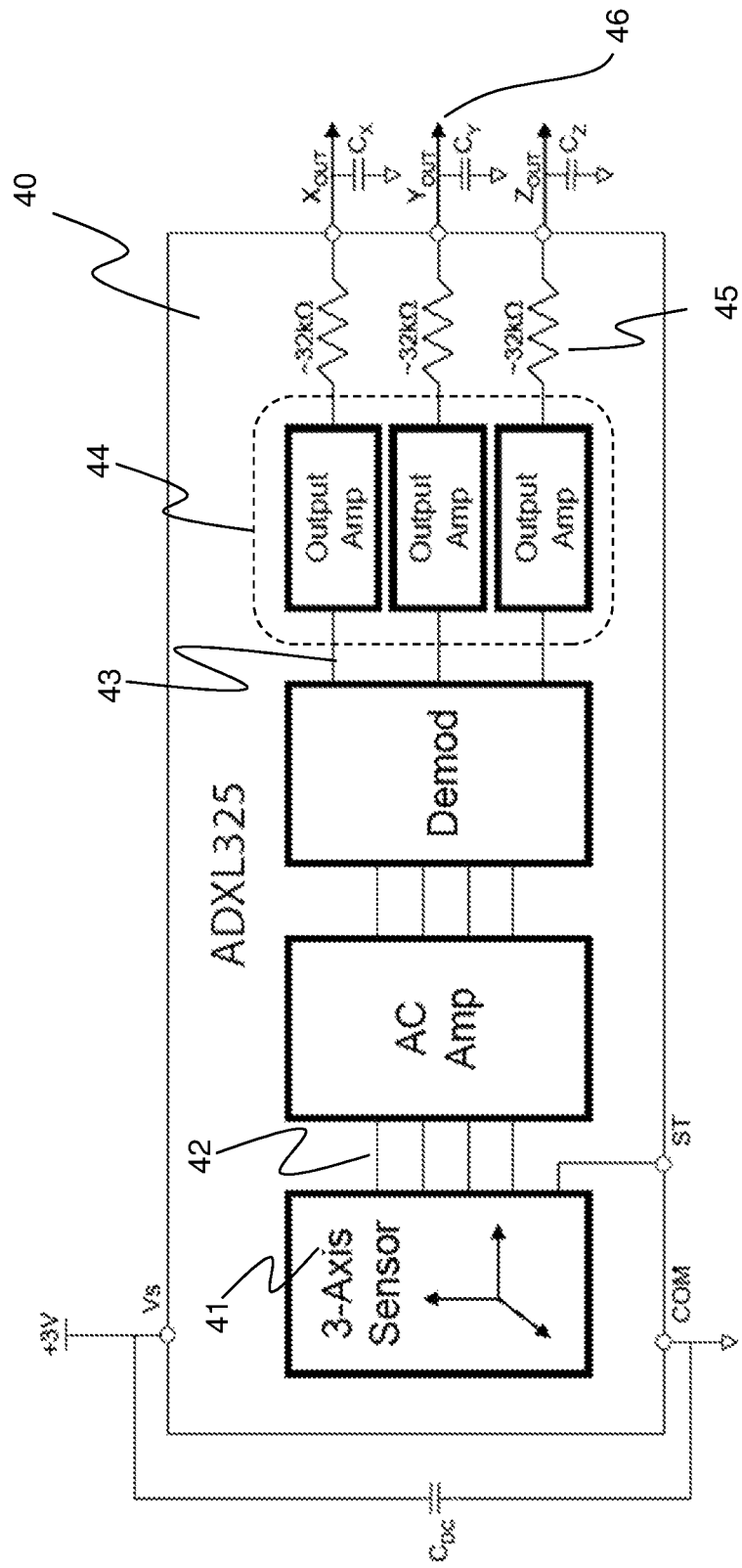

FIG. 2c is an electrical schematic diagram for one embodiment of a three-axis accelerometer of the present invention. The three-axis accelerometer system 40 contains a polysilicon surface micromachined sensor 41 and signal conditioning circuitry to implement an open-loop acceleration measurement architecture. The sensor is a polysilicon surface micromachined structure built on top of a silicon wafer. Polysilicon springs suspend the structure over the surface of the wafer and provide a resistance against acceleration forces. Deflection of the structure is measured using a differential capacitor that consists of independent fixed plates and plates attached to the moving mass. The fixed plates are driven by 180° out-of-phase square waves. Acceleration deflects the moving mass and unbalances the differential capacitor resulting in an analog sensor output 42 whose amplitude voltage is proportional to acceleration. Phase-sensitive demodulation techniques are then used to determine the magnitude and direction of the acceleration. The demodulator output 43 is amplified 44 and brought off-chip through a 32 kΩ resistor 45. The user may then set the signal bandwidth of the device by adding a capacitor 46. This filtering improves measurement resolution and helps prevent aliasing. As described for gyroscopes, any combinations and orientations of single, dual, and three-axis accelerometers may be used known to those skilled in the art in order to obtain accelerometric data in three orthogonal directions.

Figure 3:
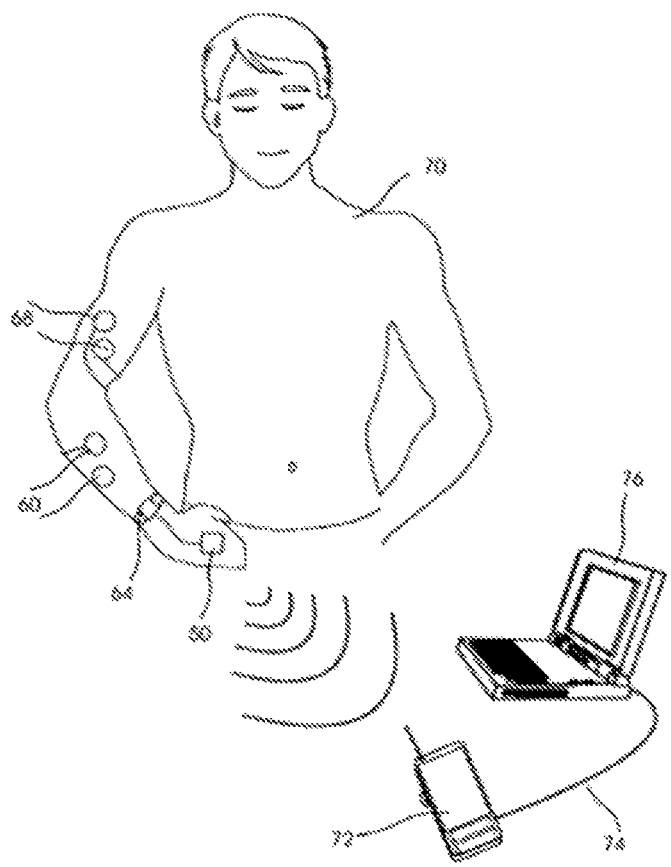
FIG. 3 Schematic showing various system components of the movement disorder recovery device as applied to a subject.

FIG. 3 illustrates one embodiment of the portable rehabilitation therapy system. The computer 76 in this embodiment can provide a stimulus such as video, audio, written or verbal instructions, or some combination thereof. The video can be as simple as a video game which the subject 70 responds to through movement of various parts of the subject's body, which are the focus of the therapy. The external sensor module 50 in this embodiment contains three orthogonal accelerometers (not shown) and three orthogonal gyroscopes (not shown). This input to the external sensor module 50 consists of the kinetic forces applied by the user and measured by the accelerometers and gyroscopes. The output from the board is linear acceleration and angular velocity data in the form of output voltages. These output voltages are input to the transceiver module 64. These voltages undergo signal conditioning and filtering before sampling by an analog to digital converter. This digital data is then transmitted as a packet in RF transmission over a radio link or through a hardwire connection to a computer. Additionally, EMG electrodes 60 worn by the subject may be input to the transceiver module. An amplifier on the transceiver module 64 amplifies the EMG signal(s) before signal conditioning, filtering, and sampling by the analog to digital converter. The EMG data is sent over a hardwire connection to a computer and/or contained in the packet for RF transmission. A microprocessor (not shown) in the transceiver module 64 controls the entire process. Kinetic and EMG data packets may be sent by RF transmission to a nearby computer transceiver 72 which receives the data using a radio connected to a computer 76 or over a hardwire connection. The computer 76 then processes, analyzes, and stores the data. The kinetic sensor board 50 measures accelerations along and angular velocities about each of three orthogonal axes. The signals from the accelerometers and gyroscopes of the kinetic sensor board 50 are preferably input into a processor for signal conditioning and filtering. Preferably, a combination of three axes of gyroscopes as discussed in FIG. 1 are utilized on the kinetic sensor board with an input range of at least 1500 degrees/second. Specific parts, the LPR5150AL and LY5150ALH (a dual and single axis gyroscope, respectively) from STMicroelectronics, were selected after an analysis of cost, size and power consumption. The land grid array type of component was selected to minimize size. Additionally, a MEMS technology three-axis accelerometer, from Analog Devices (ADXL325), was employed to record accelerations along the orthogonal x, y, and z-axes. The sensors provide full-scale range of ±5 g, low noise (250 ug/sqrt (Hz)), and low power (typically 350 uA per axis) in a surface mount package. Other combinations of accelerometers and gyroscopes known to those skilled in the art could also be used. A lightweight plastic housing was then used to house the sensor for measuring the subject's external body motion. The external body motion sensor(s) can be worn on the subject's finger, hand, wrist, fore arm, upper arm, head, chest, back, waist, legs, thighs, feet, ankles, heels, toes, and/or the like.

Various embodiments of the present invention may include a sensor(s) for measuring the subject's electrical muscle activity through techniques such as electromyography (EMG) or the like. FIG. 3 shows the EMG electrodes 60 and stimulating electrodes 68 which are connected to the transceiver or command module 64. With an EMG sensor, a voltage difference or difference in electrical potential is measured between at least two recording electrodes. The electrodes used can be any type known to those skilled in the art including both indwelling (needle), surface and dry electrodes. Typical EMG electrodes connections may have an impedance in the range of from 5 to 10 K ohms. It is in general desirable to reduce such impedance levels to below 2 K ohms. Therefore a conductive paste or gel may be applied to the electrode to create a connection with an impedance below 2 K ohms. Alternatively, the subject(s) skin may be mechanically abraded, the electrode may be amplified or a dry electrode may be used. Dry physiological recording electrodes of the type described in U.S. patent application Ser. No. 09/949,055 are herein incorporated by reference. Dry electrodes provide the advantage that there is no gel to dry out and no skin to abrade or clean. Additionally if electrodes are used as the sensor(s), preferably at least three electrodes are used—two signal electrodes and one reference electrode.

Preferably, the transceiver module 64 contains one or more electronic components such as the microprocessor 70 for detecting both the signals from the gyroscopes 51 and accelerometers 52, and for detecting the signal from an EMG electrode 60. Preferably, the one or more electronic components also filter (and possibly amplify) the detected EMG signals and kinetic motion signals, and more preferably convert these signals, which are in an analog form into a digital signal for transmission to the remote receiving unit or over the hardwire link to the computer. The one or more electronic components are attached to the subject as part of device or system. Further preferably, the one or more electronic components can receive a signal from the remote receiving unit or other remote transmitters or over a hardwire link. The one or more electronic components may include circuitry for but are not limited to for example electrode amplifiers, signal filters, analog to digital converter, radio, a DC power source and combinations thereof. The one or more electronic components may comprise one processing chip, multiple chips, single function components or combinations thereof, which can perform all of the necessary functions of detecting a kinetic or physiological signal from the electrode, uploading data to a computer through a serial link, transmitting a signal corresponding to a kinetic or physiological signal to a receiving unit, controlling an automated treatment device, communicating with a central database system, and optionally receiving a signal from a remote transmitter. These one or more electronic components can be assembled on a printed circuit board or by any other means known to those skilled in the art. Preferably, the one or more electronic components can be assembled on a printed circuit board or by other means so its imprint covers an area less than 4 in$^2$, more preferably less than 2 in$^2$, even more preferably less than 1 in$^2$, still even more preferably less than 0.6 in$^2$, and most preferably less than 0.25 in$^2$.

Preferably, the circuitry of the one or more electronic components is appropriately modified so as to function with any suitable miniature DC power source. More preferably, the DC power source is a battery. The most preferred battery of the present invention is lithium powered batteries. Lithium ion batteries offer high specific energy (the number of given hours for a specific weight), which is preferable. Additionally, these commercially available batteries are readily available and inexpensive. Other types of batteries include but are not limited to primary and secondary batteries. Primary batteries are not rechargeable since the chemical reaction that produces the electricity is not reversible. Primary batteries include lithium primary batteries (e.g., lithium/thionyl chloride, lithium/manganese dioxide, lithium/carbon monofluoride, lithium/copper oxide, lithium/iodine, lithium/silver vanadium oxide and others), alkaline primary batteries, zinc-carbon, zinc chloride, magnesium/manganese dioxide, alkaline-manganese dioxide, mercuric oxide, silver oxide as well as zinc/air and others. Rechargeable (secondary) batteries include nickel-cadmium, nickel-zinc, nickel-metal hydride, rechargeable zinc/alkaline/manganese dioxide, lithium/polymer, lithium-ion and others.

Preferably, the circuitry of the one or more electronic components comprises data acquisition circuitry further including an amplifier that amplifies the EMG, (The gyroscope and accelerometer signals will not need to be amplified.). The data acquisition circuitry is designed with the goal of reducing size, lowering (or filtering) the noise, increasing the DC offset rejection and reducing the system's offset voltages. The data acquisition circuitry may be constrained by the requirements for extremely high input impedance, very low noise and rejection of very large DC offset and common-mode voltages, while measuring a very small signal of interest. Additional constraints arise from the need for a "brick-wall" style input protection against ESD and EMI. The exact parameters of the design, such as input impedance, gain and passband, can be adjusted at the time of manufacture to suit a specific application via a table of component values to achieve a specific full-scale range and passband.

More preferably, a low-noise, lower power instrumentation amplifier is used. The inputs for this circuitry is guarded with preferably, external ESD/EMI protection, and very high-impedance passive filters to reject DC common-mode and normal-mode voltages. Still preferably, the instrumentation amplifier gain can be adjusted from unity to approximately 100 to suit the requirements of a specific application. If additional gain is required, it preferably is provided in a second-order anti-bias filter, whose cutoff frequency can be adjusted to suit a specific application, with due regard to the sampling rate. Still preferably, the reference input of the instrumentation amplifier is tightly controlled by a DC cancellation integrator servo that uses closed-loop control to cancel all DC offsets in the components in the analog signal chain to within a few analog-to digital converter (ADC) counts of perfection, to ensure long term stability of the zero reference.

Preferably, the signals are converted to a digital form. This can be achieved with an electronic component or processing chip through the use of an ADC. More preferably, the ADC restricts resolution to 16-bits due to the ambient noise environment in such chips. Despite this constraint, the ADC remains the preferable method of choice for size-constrained applications such as with the present invention unless a custom data acquisition chip is used because the integration reduces the total chip count and significantly reduces the number of interconnects required on the printed circuit board.

Preferably, the circuitry of the sensor board comprises a digital section. More preferably, the heart of the digital section of the sensor board is the Analog Devices ADUC7020 microcontroller. The Analog Devices ADUC7020 microcontroller contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry of the transceiver module comprises a digital section. More preferably, the heart of the digital section of the sensor board is the Atmel ATMEGA128 microcontroller. The Atmel ATMEGA128 microcontroller contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry for the one or more electronic components is designed to provide for communication with external quality control test equipment prior to sale, and more preferably with automated final test equipment. In order to supply such capability without impacting the final size of the finished unit, one embodiment is to design a communications interface on a separate PCB using the SPI bus with an external UART and level-conversion circuitry to implement a standard serial interface for connection to a personal computer or some other form of test equipment. The physical connection to such a device requires significant PCB area, so preferably the physical connection is designed to keep the PCB at minimal imprint area. More preferably, the physical connection is designed with a break-off tab with fingers that mate with an edge connector. This allows all required final testing and calibration, including the programming of the processing chip memory, can be carried out through this connector, with test signals being applied to the analog inputs through the normal connections which remain accessible in the final unit. By using an edge fingers on the production unit, and an edge connector in the production testing and calibration adapter, the system can be tested and calibrated without leaving any unnecessary electronic components or too large a PCB imprint area on the final unit. Preferably, the circuitry for the one or more electronic components comprises nonvolatile, rewriteable memory. Alternatively, if the circuitry for the one or more electronic components doesn't comprise nonvolatile, rewriteable memory then an approach should be used to allow for reprogramming of the final parameters such as radio channelization and data acquisition and scaling. Without nonvolatile, rewriteable memory, the program memory can be programmed only once. Therefore one embodiment of the present invention involves selective programming of a specific area of the program memory without programming the entire memory in one operation. Preferably, this is accomplished by setting aside a specific area of program memory large enough to store several copies of the required parameters. Procedurally, this is accomplished by initially programming the circuitry for the one or more electronic components with default parameters appropriate for the testing and calibration. When the final parameters have been determined, the next area is programmed with these parameters. If the final testing and calibration reveals problems, or some other need arises to change the values, additional variations of the parameters may be programmed. The firmware of various embodiments of the present invention scans for the first blank configuration block and then uses the value from the preceding block as the operational parameters. This arrangement allows for reprogramming of the parameters up to several dozen times, with no size penalty for external EEPROM or other nonvolatile RAM. The circuitry for the one or more electronic components has provisions for in-circuit programming and verification of the program memory, and this is supported by the breakoff test connector. The operational parameters can thus be changed up until the time at which the test connector is broken off just before shipping the final unit. Thus the manufacturability and size of the circuitry for the one or more electronic components is optimized.

Preferably the circuitry of the one or more electronic components includes an RF transmitter. Still preferably includes a Bluetooth™ radio. Another feature of the circuitry of the one or more electronic components preferably is an antenna. The antenna, preferably, is integrated in the rest of the circuitry. The antenna can be configured in a number of ways, for example as a single loop, dipole, dipole with termination impedance, logarithmic-periodic, dielectric, strip conduction or reflector antenna. The antenna is designed to include but not be limited to the best combination of usable range, production efficiency and end-system usability. Preferably, the antenna consists of one or more conductive wires or strips, which are arranged in a pattern to maximize surface area. The large surface area will allow for lower transmission outputs for the data transmission. The large surface area will also be helpful in receiving high frequency energy from an external power source for storage. Optionally, the radio transmissions of the present invention may use frequency-selective antennas for separating the transmission and receiving bands, if a RF transmitter and receiver are used on the electrode patch, and polarization-sensitive antennas in connection with directional transmission. Polarization-sensitive antennas consist of, for example, thin metal strips arranged in parallel on an insulating carrier material. Such a structure is insensitive to or permeable to electromagnetic waves with vertical polarization; waves with parallel polarization are reflected or absorbed depending on the design. It is possible to obtain in this way, for example good cross polarization decoupling in connection with linear polarization. It is further possible to integrate the antenna into the frame of a processing chip or into one or more of the other electronic components, whereby the antenna is preferably realized by means of thin film technology. The antenna can serve to just transfer data or for both transferring data to and for receiving control data received from a remote communication station which can include but is not limited to a wireless relay, a computer or a processor system. Optionally, the antenna can also serve to receive high-frequency energy (for energy supply or supplement). In any scenario, only one antenna is required for transmitting data, receiving data and optionally receiving energy. Optionally, directional couples can be arranged on the transmitter outputs of the remote communication station. The couplers being used to measure the radiated or reflected radio wave transmission output. Any damage to the antenna (or also any faulty adaptation) thus can be registered, because it is expressed by increased reflection values.

In any RF link, errors are an unfortunate and unavoidable problem. Analog systems can often tolerate a certain level of error. Digital systems, however, while being inherently much more resistant to errors, also suffer a much greater impact when errors occur. Thus the present invention when used as a digital system, preferably includes an error control sub architecture. Preferably, the RF link of the present invention is digital. RF links can be one-way or two-way. One-way links are used to just transmit data. Two-way links are used for both sending and receiving data.

Preferably, the RF link utilizes a two-way (bi-directional) data transmission. By using a two-way data transmission the data safety is significantly increased. By transmitting redundant information in the data, the remote communication station is capable of recognizing errors and request a renewed transmission of the data. In the presence of excessive transmission problems such as, for example transmission over excessively great distances, or due to obstacles absorbing the signals, the remote communication station is capable of controlling the data transmission, or to manipulate on its own the data. With control of data transmission it is also possible to control or re-set the parameters of the system, e.g., changing the transmission channel. This would be applicable for example if the signal transmitted is superimposed by other sources of interference then by changing the channel the remote communication station could secure a flawless and interference free transmission. Another example would be if the signal transmitted is too weak, the remote communication station can transmit a command to increase its transmitting power. Still another example would be the remote communication station to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements. This also reduces the energy requirements, thereby providing longer battery life. Another advantage of a two-way, bi-directional digital data transmission lies in the possibility of transmitting test codes in order to filter out external interferences such as, for example, refraction or scatter from the transmission current. In this way, it is possible to reconstruct falsely transmitted data.

The remote communication station of various embodiments of the present invention can be any device known to receive RF transmissions used by those skilled in the art to receive transmissions of data. The remote communication station by way of example but not limitation can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the remote communication station can further transmit data both to another device and/or back. Further optionally, two different remote communication stations can be used, one for receiving transmitted data and another for sending data. For example, with the home therapy system of the present invention, the remote communication system of the present invention can be a wireless router, which establishes a broadband Internet connection and transmits the physiological signal to a remote Internet site for analysis, preferably by the subject's physician. Another example is where the remote communication system is a PDA, computer or cell phone, which receives the physiological data transmission, optionally re-processes the information, and re-transmits the information via cell towers, land phone lines or cable to a remote site for analysis. Another example is where the remote communication system is a computer or processor, which receives the data transmission and displays the data or records it on some recording medium, which can be displayed or transferred for analysis at a later time. Another example is where the remote communication system is a computer or processor which first receives the physiological data transmission, then communicates bi-directionally with a central database system, processes the totality of received information, and lastly transmits programming signals to an automated treatment device according to a recommended treatment.

The digitized kinetic or physiological signal is then, preferably, transmitted wirelessly to a remote communication station, see FIG. 3. This remote communication station allows the subject wide movement. Preferably, the remote communication station can pick up and transmit signals from distances of greater than about 5 feet from the subject, more preferably greater than about 10 feet from the subject, even more preferably greater than about 20 feet from the subject, still even more preferably greater than about 50 feet from the subject, still even more preferably greater than about 200 feet from the subject, and most preferably greater than about 500 feet from the subject. The remote communication station is used to re-transmit the signal, reports, and/or treatment protocols based in part from the physiological signal from the remote communication station wirelessly or via the internet to another monitor, computer or processor system. This allows the physician or monitoring service to review the subjects physiological signals and if necessary to make a determination, which could include modifying the patients treatment protocols.

Optionally, the system of the present invention includes some form of instruction, which can be in written form on paper or on a computer monitor, or on a video. Preferably, a video is used which instructs the subjects to perform a series of tasks during which their kinetic motion and/or EMG can be measured. Since the system of the present invention is preferably used in the subject's home, a video giving directions and/or describing various tasks to be performed by the subject is included with the system. The video may be accessed or viewed for example but not by way of limitation through use of video tape, DVD, as part of computer software provided, through the internet, or the like. The directions could include but are not limited to instructions on how to don the device, how to turn the device on, and the like. The description of various tasks could include but is not limited to exercises which are typically used by a technician, clinician or physician to evaluate a subject with a movement disorder including but not limited to hand grasps, finger tapping exercises, other movements and the like. One embodiment of a video includes the technician, clinician or physician looking into the camera, as they would a patient, and instructing them on device setup, instructing the patients through each of the tasks to be performed, providing verbal encouragement via video after a task, and asking subject's to repeat a task if it was not completed. Preferably, these video clips are edited and converted to a MPEG files using a Pinnacle Studios digital video system that includes a fire-wire card and editing software. For movement disorders such as stroke preferably the technician, clinician or physician instructs the user through multiple tasks that would normally be completed in their in clinic therapy session. More preferably, if the video is linked to the user interface software, the software will automatically detect if a subject has performed the requested task and provide feedback through the video to either repeat the task or continue to the next task. The motions of the user may also be used to control a video game interface and determine if functional electrical stimulation is required to assist with the task.

The present invention includes various methods of measuring a subject's motion and muscle activity and using those parameters to provide feedback and control for therapy. These methods include a number of steps which may include but are not limited to measuring a subject's external body motion; transmitting wirelessly or over a hardwire link a signal based in part on the subject's measured external body motion; receiving the wirelessly transmitted signal or over a hardwire link; and providing feedback, electrical stimulation, automatic drug delivery, or other treatment protocols based in part on the signal.

Various embodiments of the present invention include a device for providing deep brain stimulation (DBS) or functional electrical stimulation (FES) to the subject. Forms of electrical stimulation are advantageous compared to other therapies since it can be non-invasive with minimal side effects. The system may utilize electrodes placed on the surface of the skin (FES) or with implanted electrodes (DBS and FES). DBS and FES electrically stimulate the brain and individual muscles respectively to create a desired reaction, such as muscle contraction or inhibition. Some movement disorder patients have paralyzed muscles while others have weak muscles that are over powered by spasticity of an opposing muscle group. Therefore, a muscle normally required for a therapy, but inactive due to a movement disorder can be included during therapy using FES. On the other hand, some movement disorder patients suffer from involuntary muscle contractions, such as tremor. In these cases, treatments such deep brain stimulation can be used to help suppress such contractions. In addition, using FES at the sensory level helps the subject to localize the muscles used for a particular therapy task. Sensory stimulation in conjunction with physiotherapy may improve motor skills. Providing feedback from the subject's own movements facilitates motor learning and may drive cortical reorganization.

The main components of an electrical stimulation system of various embodiments of the present invention are the electrodes, the stimulator (or pulse generator), and sensors or switches. When FES is being used to move muscles, current pulses in the electrodes cause the weakened or paralyzed muscles to contract. In other applications, currents in the electrodes may produce electrical currents in the tissues without moving any muscles. The stimulator controls the strength and timing of the low-level pulses that flow to the electrodes. The sensors or switches control the starting and stopping of the pulses supplied by the stimulator.

Many modes of a FES device or system can be used in the movement disorder recovery system and methods of the present invention. Two modes which are used by way of example but not limitation include 1) adaptively modulating stimulation during therapy, and 2) increase muscle strength through exercise.

One embodiment of the electrical stimulation device, unit or system of the present invention is a battery powered device. This device, as an FES unit, can deliver up to four channels of stimulation using a 3.7V Lithium Plymer rechargeable battery. Each channel can deliver electrical impulses to a different target muscle. This device uses a two-stage stimulator power supply, which multiplies the small voltages from the battery into a voltage large enough for the desired stimulation. Each stage has a charge pump which pulls the charge directly from the batteries. Stage one produces five volts, while stage two produces 60 volts and contains the high voltage section and the main power regulator for the circuit. The 60 volts is produced by the high voltage section, which is comprised of a charge pump and two 2.2 µF capacitors placed in series. Each capacitor can hold up to 35 volts of charge. A bleed-off branch funnels any excess charge from the capacitors back to the charge pump, which acts as a feedback regulator preventing the charge pump from pulling more charge from the batteries. In this way, energy is not wasted. An LED is designed into the second stage to indicate voltage. The main power regulator produces 3.3 volts for the rest of the circuit.

The stimulator is attached to an Atmel Atmega 128L microprocessor running at 8 MHz. This acts as the central control unit for the stimulator. The unit includes two serial ports, an SPI port, and multiple timers and counters. The four output channels are set on the digital to analog converter using the SPI port. The digital to analog converter drives the amplitude of the four channels in the output stage.

The output stage is where the stimulation pulse is delivered. This phase is used to charge up the capacitors, which are then discharged. This is called the cathodic stimulating phase. The capacitors are recharged during the anodic recharging phase. The digital to analog converter sets the amplitude levels for each of the four channels. The converter has eight bits of resolution, which results in 0.2 mA steps from 0 to 50 mA. This analog output (for each channel) goes through the buffer amplifiers, which in turn control the gate on the output transistor. The speed at which the charge comes off the capacitors depends on the amplitude hitting the gate of the output transistor. This speed determines the amount of the stimulating current. When the capacitors discharge, the control unit turns off the cathodic phase and enables the capacitors to recharge (the anodic phase). During recharging, the control center connects the high voltage section to the output capacitor through a current-limiting FET circuit.

Another example of a battery powered electrical stimulation device may be a deep brain stimulation (DBS) unit. DBS units, powered by a rechargeable lithium-ion battery unit, can deliver stimulation to 1 or 2 leads which are generally implanted in the subthalamic nucleus, globus pallidus interna, or ventro intermediate nucleus of the thalamus. A typical implanted DBS stimulation lead consists of a thin insulated needle comprising four platinum/iridium electrodes spaced 0.5 or 1.5 mm apart along the length of the lead. One or multiple leads may be implanted in a target brain region or regions to provide symptom-inhibiting high-frequency stimulation, although some research suggests that excellent results can be achieved even when the lead is implanted distant from a target region. A DBS lead is connected to an implantable pulse generator (IPG), which serves as a controller and power source, via an extension cable tunneled subcutaneously to a subcutaneous pocket in the chest or abdominal cavity. The IPG typically includes the rechargeable lithium-ion battery and circuitry for telemetered communication with an external programming device used to adjust, or "tune," DBS lead stimulation parameters, which may include stimulation frequency, amplitude, pulse width (or wavelength), and contact configuration (that is, the selection of which electrodes are utilized from among the four electrodes available on a lead, and, if two or more electrodes are active, the relative polarity of each). These parameters are initially set during implantation surgery and are then further fined-tuned in the outpatient clinic or in a doctor's office following surgery to maximize therapeutic benefit and minimize undesirable stimulation-induced side effects. The first such tuning session usually takes place several weeks following implantation surgery, after the patient has recovered and inflammation at the lead placement site has subsided.

Initial DBS parameters are generally set for a pulse width of 60 microseconds and a frequency of 130 Hz. Stimualtion is then "turned on" and the amplitude incremented to a clinical level until subject symptoms begin to disappear. After an effective amplitude is found, the other parameters may also be tuned to further optimize the DBS settings. During the tuning process, the DBS unit allows pulse width to vary from 60 to 450 microseconds with a 10 microsecond resolution, however, typical values are usually kept between 60 and 120 microseconds. Frequency can be set from 2 to 250 Hz with a 5 Hz resolution, but generally only higher frequencies (over 100 Hz) show positive results, therefore general settings are usually between 130 and 185 Hz. Amplitude can range from 0 to 10.5 volts with a 0.05 volt resolution (the full range of amplitudes includes the negative values to account for both anodic and cathodic configurations of electrodes), however, the 1 to 3.5 V range is generally most acceptable (more specifically, 2.5-3.5 V for subjects with Parkinson's Disease). Additionally, in some embodiments, the DBS unit may be current controlled, meaning the amplitude of the stimulation is a current rather than a voltage. In these cases, the amplitude can range from 0 to 25.5 milliamps with a 0.1 mA resolution.

The components of the unit, including the battery and integrated circuits, are hermetically sealed within an oval-shaped titanium case in order to protect it from body fluids. The case can also have an external insulating coating to help minimize possible skeletal muscle stimulation at the implant site. One side of the unit, however, remains uninsulated so that it may serve as the positive electrode when using a unipolar configuration. The unit also contains octapolar in-line connectors for each electrode extension and multiple timers and counters.

While a wireless device(s) is the preferred for the present system, the portable therapy system may also be a tethered system or a partially tethered partially wireless system.

FIG. 4a is a block diagram showing one embodiment of the movement disorder recovery system of the present invention. The portable therapy rehabilitation system 91 of the present invention preferably comprises three modules or components: a sensor module 90, a command module 92 and a computer or processor 94. The sensor module 90 preferably further comprises at least one gyroscope 100 or other form of motion sensor, an EMG electrode(s) 102, and a stimulating or functional neuromuscular stimulating device 104. The command module 92, to which the sensor module 90 is hardwired 126 enables the signals from the sensors 100, 102 showing the subject's movement to be processed and transmitted to a computer 94. The command module 92 can also be used to either relay or calculate when to apply functional neuromuscular stimulation through the stimulating electrode 104. The command module 92 preferably comprises a system control and power supply 110 for those devices worn by the subject, functional neuromuscular hardware 112 described earlier in the application, EMG amplifiers 114, data acquisition electronics 116 and optionally a radio transceiver 118. Preferably, the command module 92 communicates with a computer or display device 94 via wireless two way radio communication 120 or a tethered, two way serial communication 122 port on each of the modules 92, 94. If a computer is used preferably, the computer comprises processing software 130, a video display 132, auditory stimulus 134 and a radio transceiver 136 or serial port (not shown).

FIG. 4b is a block diagram showing another embodiment of the movement disorder recovery system of the present invention. The portable therapy rehabilitation system of the present invention preferably comprises three modules or components: a sensor module 142, a command module 144 and a computer or processor 146. The sensor module 142 preferably further comprises at least one gyroscope 148, accelerometer 150, or other form of motion sensor, and an automated treatment device 152, such as an electrical stimulation device, automatic medicine titrator, or automatic drug delivery system. The command module 144, to which the sensor module 142 is hardwired 154 enables the signals from the sensors 148, 150 showing the subject's movement to be processed and transmitted to a computer 146. The command module 144 can also be used to either relay or determine when and how to program the automated treatment device 152. The command module 144 preferably comprises a system control and power supply 156 for those devices worn by the subject, the automated treatment device hardware 158 described earlier in the application, data acquisition electronics 160 and optionally a radio transceiver 162. Preferably, the command module 144 communicates with a computer 146 via wireless two way radio communication 164 or a tethered, two way communication 166 port on each of the modules 144, 146. If a computer is used preferably, the computer comprises processing software for correlation algorithms 168, a central database 504, and a radio transceiver 172 or communication port (not shown).

Various embodiments of the present invention that include a central database system may consist of one or many databases specialized to certain forms of patient and/or movement data, such as patient demographics, treatment history, disorder details, recorded movement data, current treatment protocols, movement scores, and the like. Movement scores are not simply meant to be a rescaling of a measured quantity. Rather, preferably they should be representative of a score that a skilled clinician might give to the subject during a movement analysis exam in the clinician's office using a standardized scale such as the Unified Parkinson's Disease Rating Scale (UPDRS). The central database or databases may be located locally or remotely with respect to a single patient or clinician. Further, the database may be part of another computer system, but is preferably run by a dedicated processor or group of processors. Preferably, all databases will also be located remotely so as to maximize the access by clinicians and patients from medical disorder fields and locations, thereby increasing an algorithm's ability to correlate data and determine a most customized treatment. More preferably, all databases will be adaptive to new patient information, and will grow in size as their use increases, thereby increasing the effectiveness of correlation algorithms as they have more information to compare and contrast with. The database system may be of any framework readily known to those skilled in the art, such as SQL, XML, or the like, so as to allow for relational queries between the databases and correlations with outside data.

Any database or database system of the present invention should comply with the Health Insurance Portability and Accountability Act (HIPAA) of 1996, particularly Title II of the act, which covers the privacy of protected patient and subject health care information. Protected information may be any part of the subject's medical record or payment history which may be linked to the individual. Such information related to this invention may include patient demographics, health history, recorded movement data, past and current treatment protocols, clinician notes, patient disorder diaries. All data may only be obtained and stored with HIPAA compliant subject authorization. In compliance with the Privacy Rule of Title II, all subjects with data in the database(s) would be able to recover their stored information, or correct any incorrect information. Furthermore, all database workers and administrators should be trained in procedures relating to protected health information, and a privacy official and contact person will be appointed to handle all protected health information concerns.

In compliance with the Security Rule of Title II for electronic protected health information, administrative, physical, and technical safeguards should be implemented to protect sensitive health information. Administrative safeguards should comprise a written set of privacy procedures referencing a privacy officer and management oversight, describing who has access to protected information, how information is restricted to the fewest number of individuals, contingency plans, and internal audits. Preferably, multiple compliance officers will be hired; only researchers and clinicians will have access to the data, and in many instances, such access should be blind during research; and internal audits will occur at a regular frequency, where regular frequency preferably means once every year, more preferably once every month, even more preferably once every week, and most preferably once every day. Physical safeguards should govern hardware of the database system, access to the equipment and software of the system, and policies regarding workstation use. Preferably, the database hardware, such as the data storage drives, will be maintained in a private, continuously secured building and more preferably in a locked sever room within a private, continuously secured building where only database administrators have access to the hardware. Technical safeguards will comprise encryption techniques for the transfer of data, authentication techniques, records of all network settings, and documented risk analysis and risk management programs. Preferably, encrypted passwords are required used for any access of the database(s), cookies and IP address tracking are used to monitor remote access, a firewall installed on the database system is used to limit inbound and outbound traffic.

The above implementations regarding HIPAA compliance are not meant to be limiting or all inclusive. Instead they are meant to outline some of the primary procedures which will be installed in order to fully comply with the act. All required procedures described in the United States Code and Code of Federal Regulations should be implemented. It is also noted that Subtitle D of the Health Information Technology for Economic and Clinical Health (HITECH) Act, enacted in 2009, extends the privacy and security provisions of HIPAA to business associates of entities using the present invention. Preferably, additional safeguards should also be taken, and every implemented procedure should be continually monitored for technological advances and/or security breaches.

Figure 5:
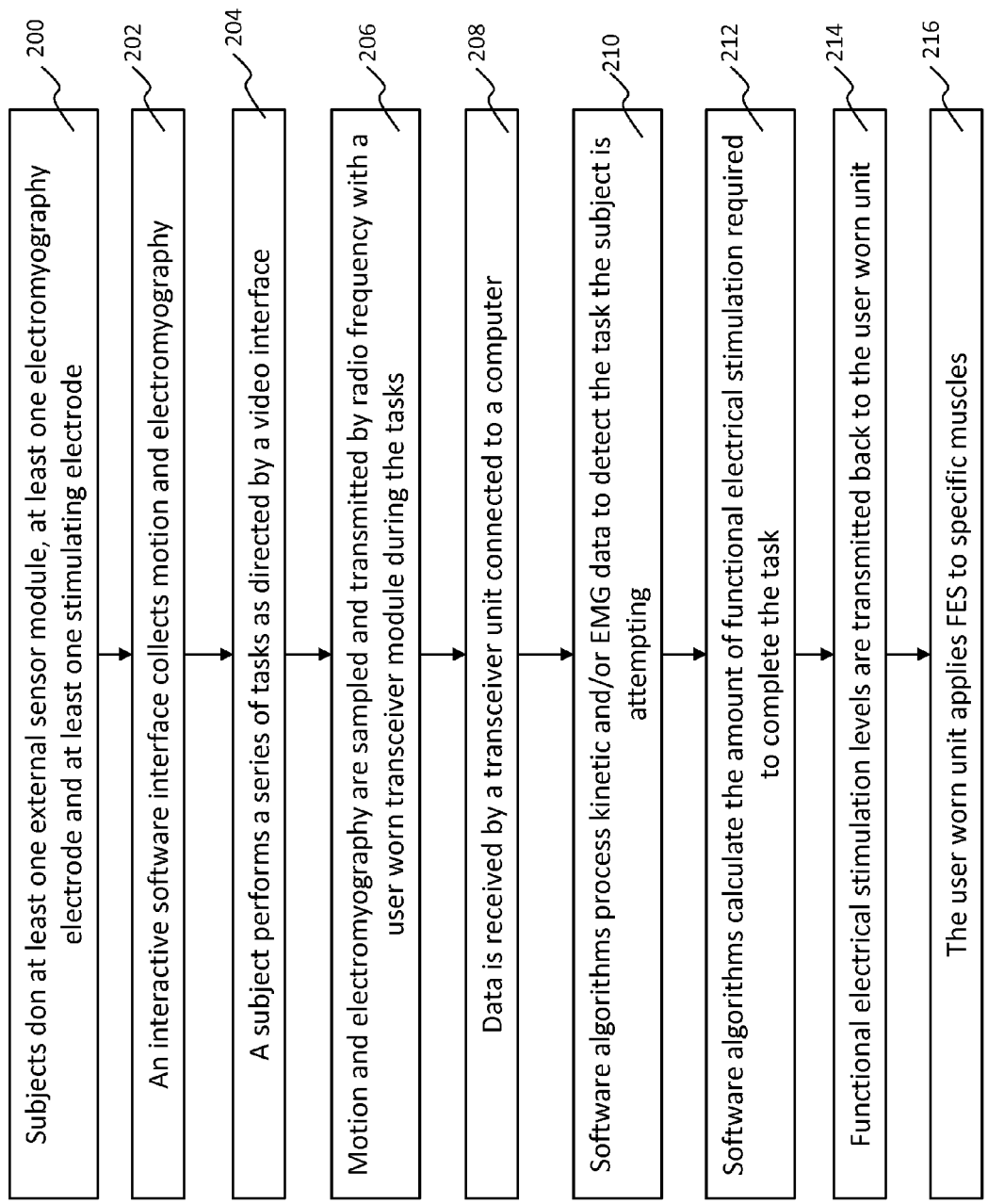
FIG. 5. Operational flow diagram showing one embodiment of the movement disorder recovery method with electrical stimulation control.

FIG. 5 is an operational flow diagram showing one embodiment of the movement disorder recovery method of the present invention with electrical stimulation control. In this embodiment, the subject dons at least one external sensor, at least one EMG electrode and at least one stimulating electrode 200. An interactive software interface collections motion and EMG signals 202. The subject is provided a stimulus such as a video requiring the performance of a series of tasks as directed by a video interface 204. Motion and electromyography are sampled from the subject and transmitted to a computer by a radio transceiver module worn by the subject during these tasks 206. Data is received by a transceiver unit connected to or part of the computer 208. Software algorithms in the computer calculate the amount of functional neuromuscular stimulation required to complete the task 210. Functional neuromuscular stimulation levels are transmitted back to the subject worn device 212. The subject worn unit then applies electrical stimulation to specific muscles 214.

Figure 6:
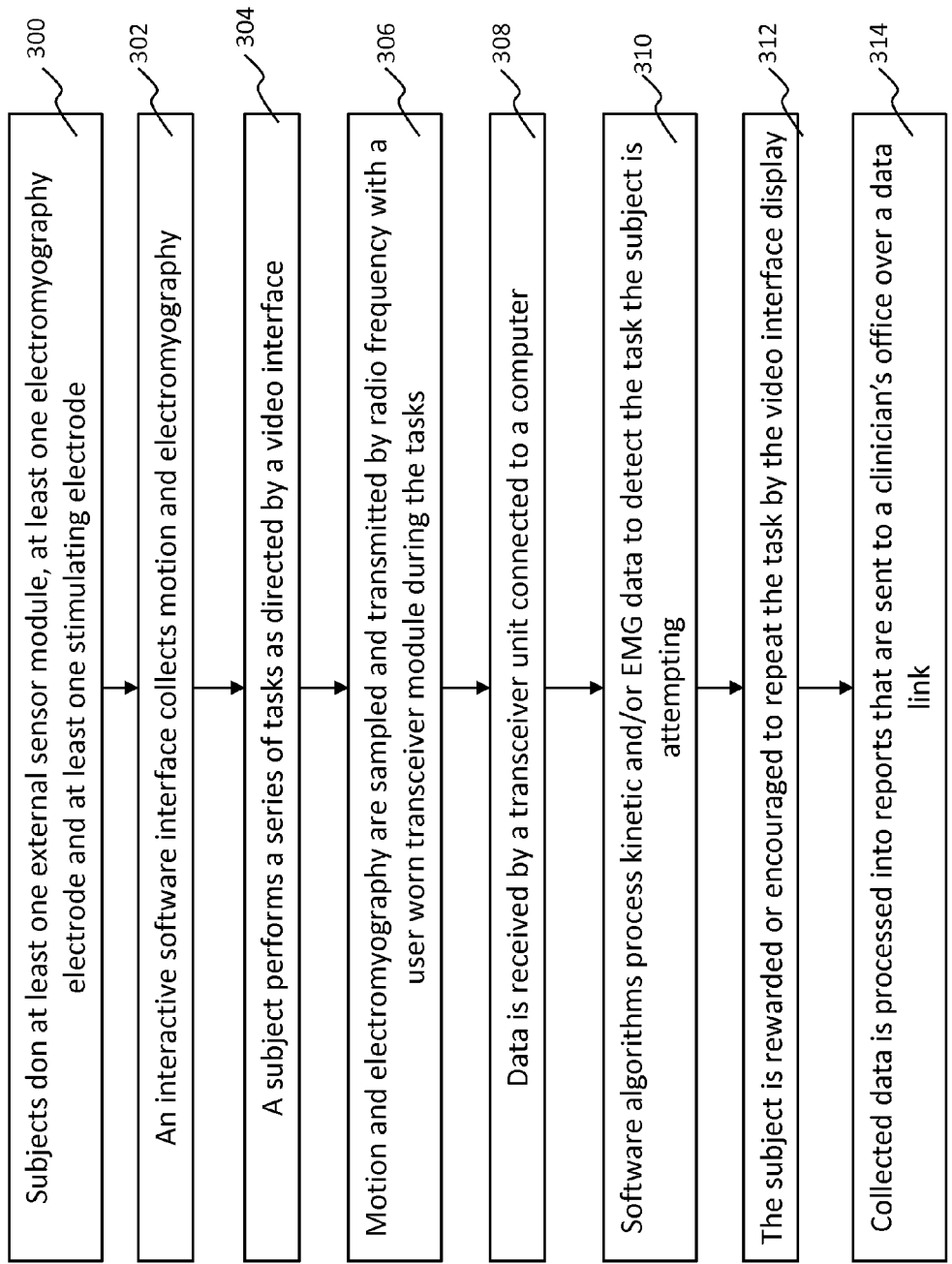
FIG. 6. Operational flow diagram showing one embodiment of the movement disorder recovery method highlighting the patient feedback and system reporting.

FIG. 6 is an operational flow diagram showing another embodiment of the movement disorder recovery method highlighting the patient feedback and system reporting. In this embodiment, the subject dons at least one external sensor, at least one EMG electrode and at least one stimulating electrode 300. An interactive software interface collections motion and EMG signals 302. The subject is provided a stimulus such as a video requiring the performance of a series of tasks as directed by a video interface 304. Motion and electromyography are sampled from the subject and transmitted to a computer by a radio transceiver module worn by the subject during these tasks 306. Data is received by a transceiver unit connected to or part of the computer 308. Software algorithms in the computer calculate the amount of functional neuromuscular stimulation required to complete the task 310. The subject is rewarded or encouraged to repeat the task by the video interface display 312. Collected data is processed into reports that are sent to a clinician's office over a data link 314.

Figure 7:
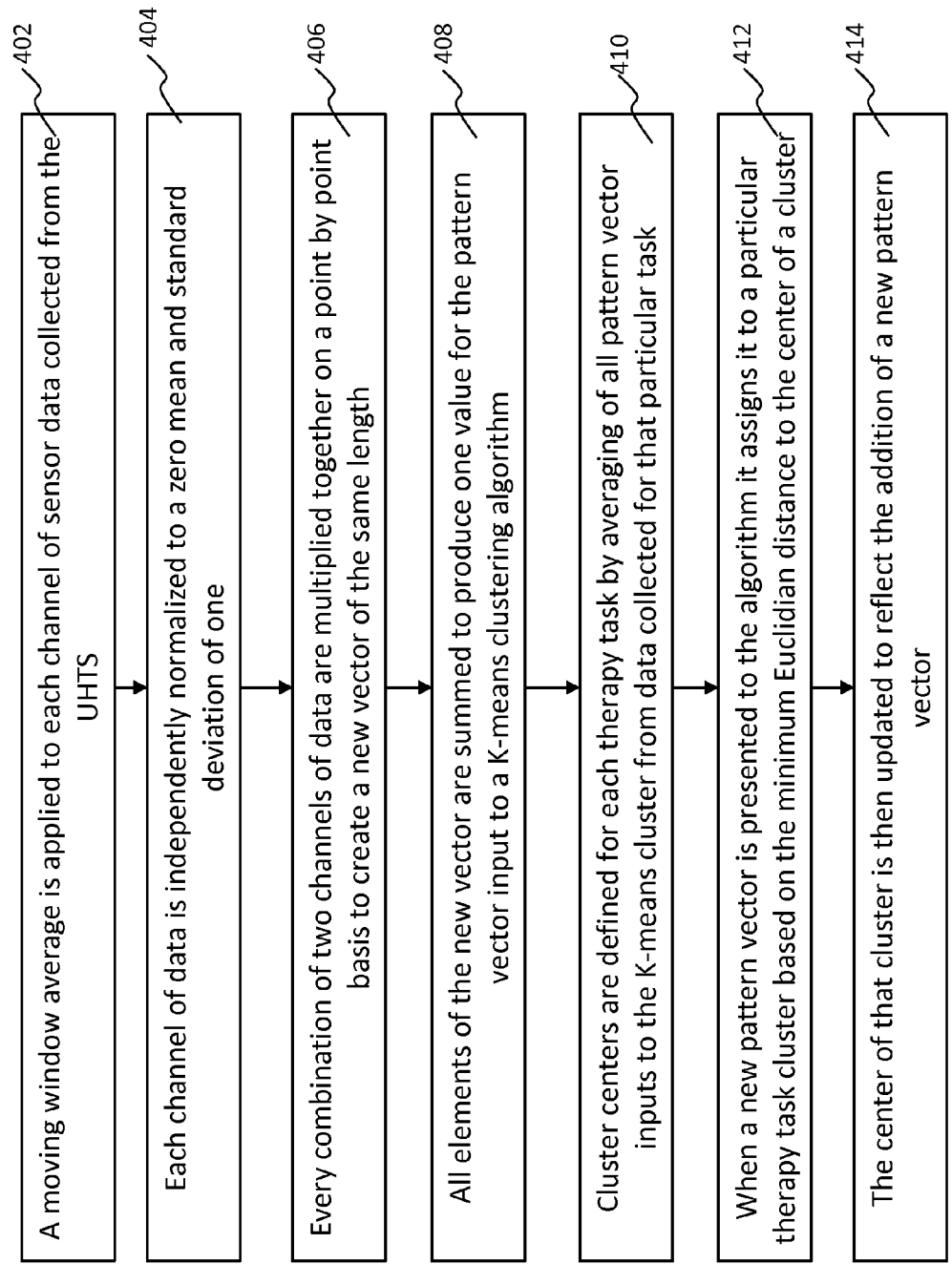
FIG. 7. Block diagram showing an algorithm for automatically detecting the therapy task that a subject is performing.

FIG. 7 is a block diagram showing one embodiment of an algorithm for automatically detecting the therapy task a subject is performing. In FIG. 7, the system software integrates algorithms for automated detection of a therapy task (FIG. 7) a person is performing for real-time subject feedback about repetitions and/or task time remaining. The algorithm uses inputs from different combinations of EMG, accelerometers, and/or gyroscopes to automatically classify therapy tasks performed by a subject. One very important difference in stroke subjects, for example, compared to normals is that we not only need to detect when they "are" performing a task, but also when they are "attempting" to perform a task. For further example, someone who cannot yet move their wrist joint may produce repeatable patterns in elbow muscles as they are "attempting" to move their wrist. Different stroke subjects will have different remaining voluntary muscles sets based on their specific injury. Therefore, large variations in coordinated muscle activity may exist between subjects for the same therapy task as well as some variation within a single subject. The algorithm allows generalization of features to produce high accuracy task discrimination.

Each subject may have unique remaining voluntary muscles and coordination patterns. It would not be reasonable to assume that a single, hard coded algorithm could be developed to distinguish tasks among every potential subject. Therefore, instead of a hard coded algorithm, the system includes an algorithm structure that can be quickly trained in a clinician's office during a single office visit while the subject completes therapy tasks as part of their normal visit.

Additionally, it is important to remember that the goal is for these subjects to improve motor control over time. Therefore, as they use the system more and more, coordination patterns of motion and EMG should continue to change, albeit slowly. Therefore, the algorithm structure should adaptively learn over time while the subject's motor function improves. Finally, the algorithm takes advantage of the fact that the therapy exercises are repetitive motions. These repetitive motions should produce specific patterns in a subset of the signals being recorded.

The algorithm utilizes a K-means clustering algorithm. The K-means algorithm provides many advantages including fast training and the ability to continue to add new data over time to adaptively learn improving subject coordination patterns. The K-means algorithm defines a set of cluster centers of n-dimensions where n is the number of quantitative input features used to describe a task trial. Once the cluster centers are defined the n quantitative features of a single trial are compared to each of the cluster centers. The Euclidean distance of all the quantitative features is calculated to each cluster center. The trial is then assigned to the cluster center that has the closest Euclidean distance. That cluster center is then updated to reflect the additional value added to it.

Quantitative input features are extracted for each therapy task completed by a subject. The following quantitative feature inputs are extracted from the system sensors for the K-means algorithm. Each signal was moving window averaged. Next, each channel for each trial was independently normalized to a zero mean and standard deviation of one. In other words, normalization for a particular data channel and trial depended only on that channel and trial. This achieved two goals. First it eliminated the need for a general normalization to maximum and minimum values collected in a calibration routine. Secondly, it did not penalize muscle activity for being of small amplitude. Next, every combination of channels was multiplied together on a point-by-point basis to create a new vector of the same length. That new vector was then summed to create one K-means input. This technique proved valuable as it described if muscles acted agonistically or antagonistically during a therapy task. If muscles act as agonists it produces very large positive numbers. If they act as antagonists, it produces very large negative numbers. Little positive or negative correlation between the muscles produces numbers closer to zero.

Initial cluster centers are defined for each task by calculating the average of the pattern vectors for data collected for each task during system training New patterns are assigned to particular clusters based on their Euclidean distance from the cluster center. New pattern vectors are assigned to the cluster whose center is the closest Euclidean distance away.

The motion and EMG patterns a subject generates for a particular therapy task will likely change as motor recovery occurs. However, these changes should take place slowly over time. Therefore, the algorithm for task classification needs to adaptively learn the new coordination patterns of a subject. Due to the fact that recovery occurs slowly, the clustering algorithm adaptively updates the cluster centers each time a new pattern is added during system use. In one embodiment of the algorithm represented by FIG. 7, a moving average is applied to each channel of sensor data collected 402, then each channel of data is independently normalized to a zero mean and standard deviation of one 404, then every combination of two channels of data are multiplied together on a point by point basis to create a new vector of the same length 406, this is followed by all the elements of the new vector being summed to produce one value for the pattern vector input to a K-means clustering algorithm 408, next cluster centers are defined for each therapy task by averaging all the pattern vector inputs to the K-means cluster from data collected for that particular task 410, when a new pattern vector is presented to the algorithm it assigns it to a particular therapy task cluster based on the minimum Euclidean distance to the center of the cluster 412, and finally the center of that cluster is updated to reflect the addition of a new pattern vector 414.

Various embodiments of the present invention may also include an algorithm to correlate current patient data with a central database system in order to determine a customized treatment for the patient. Many forms of algorithms are known to those skilled in the art for pattern matching and determining customized outputs given a set of data input, for example, one or more of a simple or multiple linear regression, an artificial neural network, an optimization algorithm, a Bayesian network, or a genetic algorithm. Preferably, the present invention utilizes an artificial neural network or optimization network. Artificial neural network may refer to a perceptron, multilayer perceptron, or the like. Optimization algorithm may refer to the simplex algorithm, or the like, known to those skilled in the art to produce an optimized output given real constraints. Other algorithms may also include decision trees or K-means clustering. More preferably, the algorithm is a feedforward artificial neural network and is trained through backpropagation techniques. By feedforward neural network, preferably the information moves in only one direction through the artificial neural network, and does not form a closed-loop between the output of the artificial neural network and one of its layers. Backpropagation learning preferably refers to altering the weights of each connection in the artificial neural network based on the resulting error after a piece of information is processed, whereby anticipated results are derived from previous patient data located in a central database. Even more preferably, the feedforward and backpropagation artificial neural network is in the form of a multilayer perceptron consisting of at least an input layer, a hidden layer, and an output layer. Most preferably, any training technique should train the algorithm using information from an adaptive central database, including, but not limited to, former patient movement data, their treatment protocols, and treatment results, in order to increase the effectiveness of its outputted treatments.

There are several aspects of utilizing an artificial neural network like the one just described that will help generate a more robust algorithm. First, pattern recognition will identify complex data trends, such as those generated by many input variables regarding subject data, not achievable by analyzing individual subject data or linear functions. Second, one of the primary advantages of an artificial neural network over linear algorithms to predict output variables is its parallel nature such that if one component fails the network can still generate an output. Third, its adaptive nature not only considers static outcome measures from individual assessments, but also dynamic interactions between these variables, allowing the algorithm to train and determine treatment recommendations as the subject's symptoms change with respect to time. Lastly, an artificial neural network can automatically modulate layer weights based in part on subject data which continuously populates a central database as part of an adaptive learning structure.

Preferably, such an algorithm will be trained with a training set that only includes subject data where treatment was successful. This will allow the algorithm to generate patient-specific treatment protocols based on the effective treatment regimens from a large database or database system of other subjects. Preferably subject data will only be included in the training set if motor scores decrease by more than 10%. More preferably, subject data will only be included in the training set if motor scores decrease by more than 25%. Even more preferably, subject data will only be included in the training set if motor scores decrease by more than 50%. Most preferably, subject data will only be included in the training set if motor scores decrease by more than 75%. Once the training set has been determined, the artificial neural network will be trained through a supervised learning process using algorithm inputs, such as patient demographics, treatment history, disorder details, recorded movement data, current treatment protocols, movement scores, and the like, and matched outputs, such as recommended treatment protocols including stimulation parameters. Preferably, a stepwise regression will be performed to determine the combination of input variables that output treatment protocols which are highly correlated to clinician treatments for subjects with successful outcomes. By highly correlated, preferably the correlation coefficient is greater than 0.25. More preferably, the correlation coefficient would be greater than 0.50. Even more preferably, the correlation coefficient would be greater than 0.80. Still more preferably, the correlation coefficient would be greater than 0.90. Most preferably, the correlation coefficient would be greater than 0.95. During this process, unit weights from each neural network layer will preferably be automatically adjusted to minimize the error between the predicted and actual treatments. The final set of input variables and neural network layer weights will be used to test the neural network's ability to generalize data. This will be done using a "one left out" technique where the training data consisting of all but one subject will be used to solve for the neural network weights. The "left out" subject will then be input to the neural network to generate predicted treatments. This process will be repeated for each subject. Preferably, success criteria of at least 80% agreement between the treatment estimation output and the final clinician selection will be determined separately for each element of the treatment protocol, such as the contacts voltage, frequency, and pulse width of an electrical stimulation protocol. More preferably, the success criteria will be at least 90% agreement between the treatment estimation output and the final clinician selection. Most preferably, the success criteria will be at least 95% agreement between the treatment estimation output and the final clinician selection.

Using such an algorithm, various embodiments of the present invention may include an output or determine medical delivery device treatment protocols. Forms of output may include a monitor displaying new treatment information to the patient, alarms, updated electronic patient records, email messages to the clinician suggesting new treatment protocols, or the like. New treatment protocols may also be automatically programmed to medical delivery devices already implanted in the patient such as electrical stimulators for deep brain stimulation or functional electrical stimulation, automated titration and drug delivery devices, or the like. In the case of electrical stimulation, such protocols may include the determination of electrical pulse parameters characterized by amplitude (volts), current (amps), frequency (Hz), and pulse width (microseconds), followed by the automated programming of a pulse generator placed beneath the skin on the chest or worn externally. For drug delivery devices, such parameters may include titration concentrations, drug titrations, doses and times.

Figure 8:
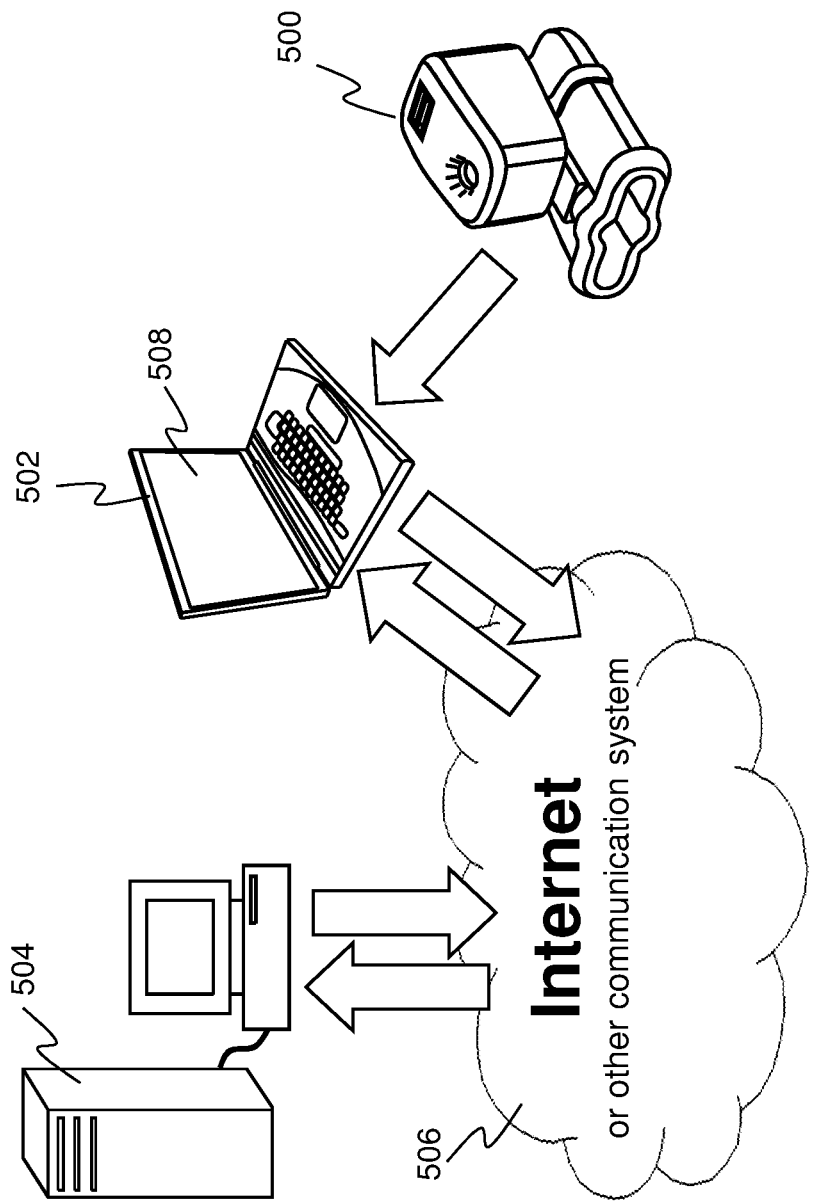
FIG. 8. Graphic depiction of data flow between sensors, processor, and adaptive central database.

FIG. 8 illustrates one embodiment of a general data relationship between patient worn sensors, a processor, and an adaptive central database. A movement measuring apparatus, comprising at least one sensor 500 is worn by a subject (not shown) and records movement data while activated. The at least one sensor 500 is preferably an accelerometer, a gyroscope, or more preferably, a combination of the two, as previously described in this application. The recorded movement data 604 is then either preprocessed or transferred directly to a processor 502 for further processing. The processor 502 uses a trained algorithm to correlate the subject's movement data with a central database 504, or database system (not shown). Communication with the central database 504 can be in any form, wired or wireless, as described above or known to those skilled in the art. FIG. 8 illustrates the communication system as the internet 506, however, this is merely by way of example, and meant to represent wireless communication as whole. As the processor 502 uses a trained algorithm to correlate data and optimize a custom treatment for the subject, data is continually sent from the processor 502 to the central database 504 and from the central database 504 to the processor 502 for the purposes of updating the database with the subject's newly recorded movement data 604, retrieving previous patients' movement and treatment information from the database, and determining an optimized and custom treatment for the subject. Once the processor 502 and central database 504 contain the subject's new customized treatment, the subject 530 or a third party, such as a clinician 520, can be alerted to or retrieve the customized treatment from an output monitor 508 on the processor 502 or via outside communication through the internet or other communication system 506 with central database 504.

Figure 9:
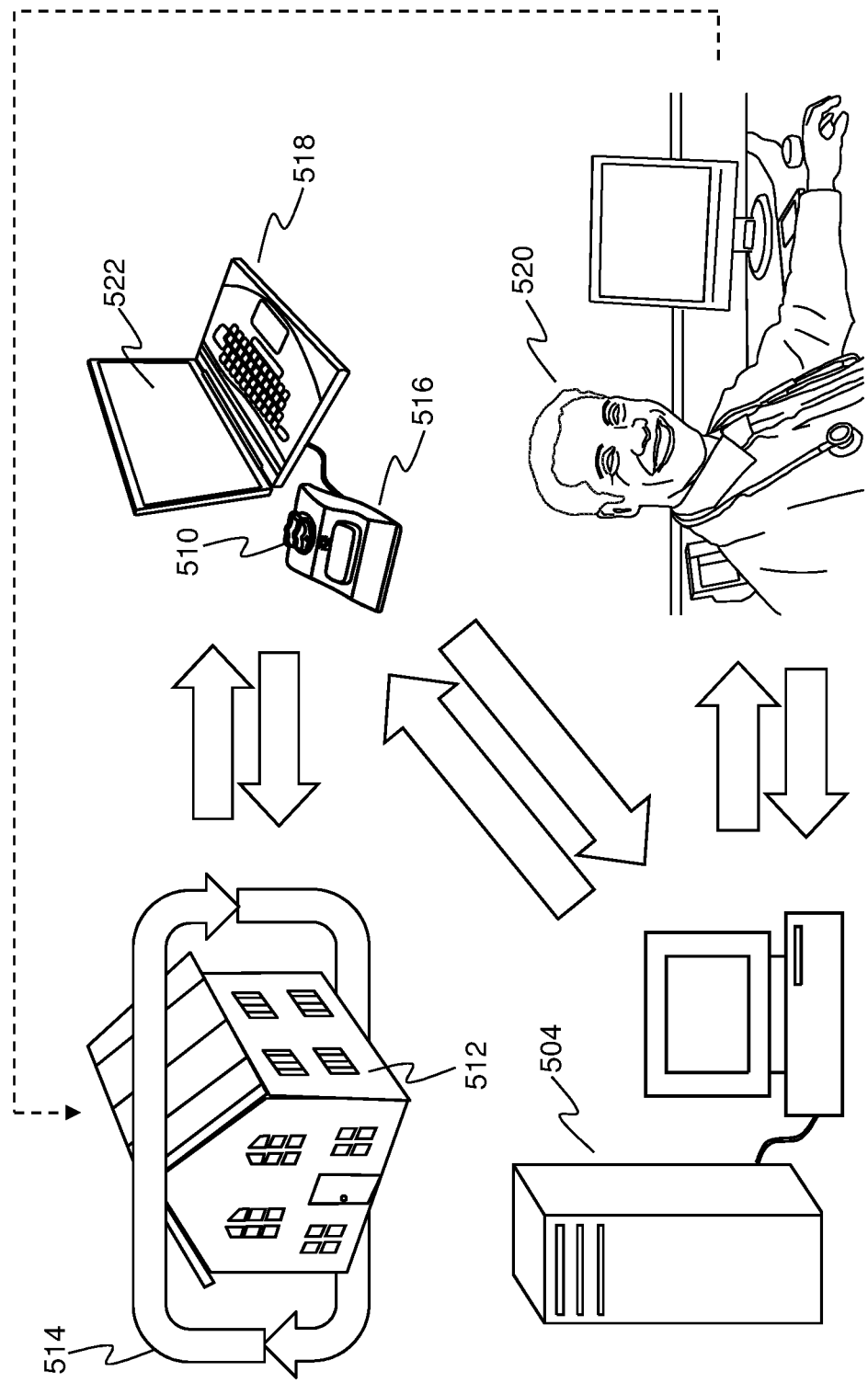
FIG. 9. Graphic depiction of continuous home movement recording and treatment tuning with the ability for remote clinician intervention.

FIG. 9 illustrates another embodiment of a general data relationship between patient worn sensors, a processor, and an adaptive central database as shown in FIG. 8. A subject (not shown) inside the home 512 or at another location wears a movement measuring apparatus 510 while performing activities of daily living inside his home 512. While performing the activities, the movement measuring apparatus 510 continually records 514 the subject's movement data. The movement measuring apparatus 510 in this embodiment can then be docked at a docking station 516, which transfers the subject's recorded movement data 604 to a processor 518 via any wired or wireless connection known by those skilled in the art. Using a trained algorithm, the processor 518 can correlate the subject's continuously recorded movement data 604 with a central database 504, or database system (not shown) to determine a custom treatment. Once the processor 518 and central database 504 contain the subject's new customized treatment, a remote third party, such as a clinician 520, can be alerted to or retrieve the customized treatment from the central database 504 via the internet or other communication system. The clinician 520 may then intervene and prescribe a new treatment based on movement data from the central database 504. Additionally, the processor 518 may output the new recommended treatment on a screen 522 for the subject to see, who may then begin the new treatment without clinical intervention.

Figure 10:
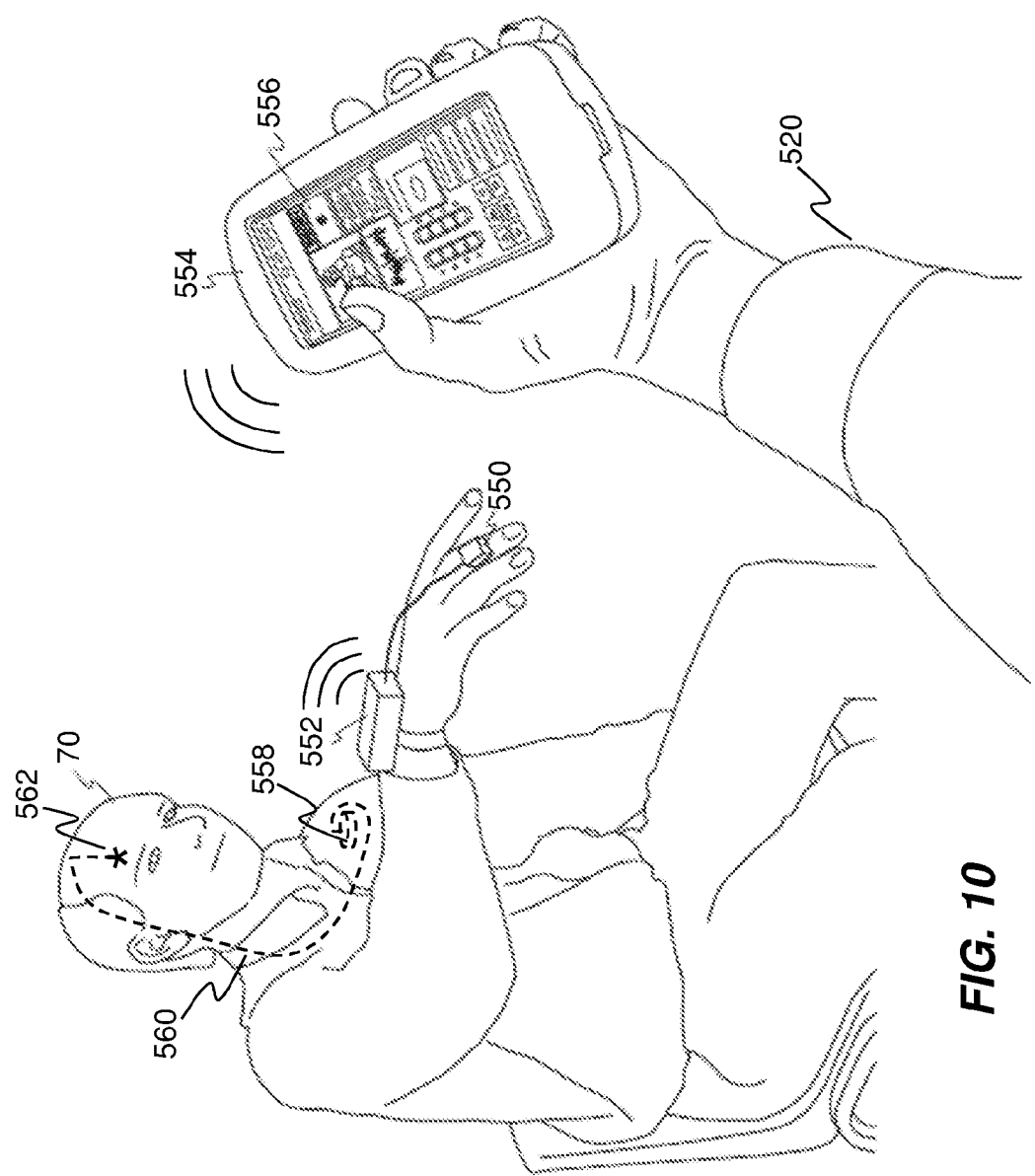
FIG. 10. Graphic depiction of clinical deep brain stimulation parameter tuning using recorded movement data and a recommended treatment protocol.

FIG. 10 illustrates a more specific embodiment of the patient customized and adaptive movement recovery system and method of improving the functional motor recovery of a subject with a movement disorder shown in FIGS. 8 and 9. Initially, a combined processor and deep brain stimulation programming device 554 is programmed by a clinician 520 to contain patient demographics, treatment history, disorder details, current treatment protocols, and the like. The device 554 uses these inputs as constraints to select appropriate trained algorithms and databases for the subject's condition. Next, a movement measuring device, worn by a subject 530, and comprising a sensor module 550 and transceiver unit 552 measures the subject's movement data during clinical tests ordered by the clinician 520. The data can be preprocessed or immediately transmitted to a combined processor and deep brain stimulation programming device 554. The processor (not shown) of the combined device 554 uses the recorded movement data to correlate with the selected central database or database system (not shown) through a wired or wireless communication system 506, such as the internet, or the like. Using a trained algorithm, the processor of the combined device 554 can determine a custom deep brain stimulation treatment protocol for the subject 530 based on a single data set or based on changes in the subject's movement data over time. Once the algorithm has determined such a recommended treatment, it is displayed on the screen of the deep brain stimulation programming device 556. The clinician 520 can then accept or reject the recommended treatment. If the treatment is accepted, the programming device transmits the necessary programming signals, via WIFI, Bluetooth, magnetic transduction, or any other protocol known to those skilled in the art and compatible with the electrical stimulation device, to the implanted pulse generator 558. The implanted pulse generator 558 then sends an electronic pulse through an implanted wire and electrode lead 560 to generate a stimulus 562 in the subject's brain according to the new treatment protocol.

Figure 11:
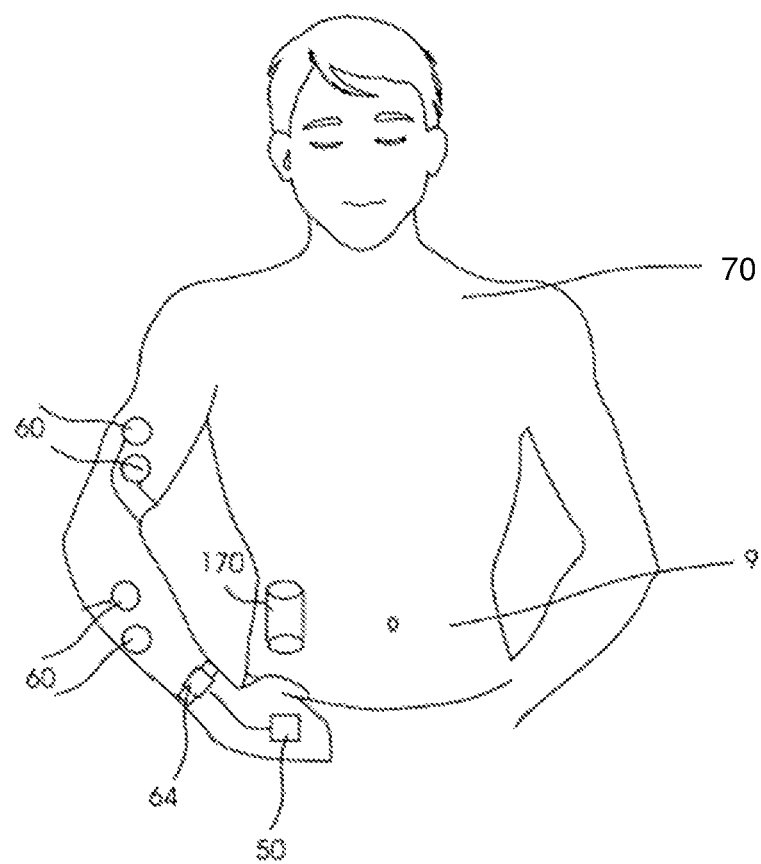
FIG. 11. Schematic showing placement of various components of closed loop drug delivery system with an implantable reservoir.

FIG. 11 is a schematic diagram showing placement of various components of closed loop drug delivery system with an implantable reservoir. In FIG. 14, the subject 70 is wearing a closed loop drug delivery system. The closed loop drug may have an external sensor module 50, a subject worn transceiver module 64, EMG electrodes 60, a reservoir 170 for holding medication with an embedded transceiver and processor and actuator for allowing delivery (not shown), a central database or database system, and a controller for activating and deactivating the actuator based in part on the signal from the at least one of the sensor modules 50. In this example a reservoir 170 being implanted into the abdomen 9 of the subject. The reservoir 170 containing medication, which is released into the subject's body through activation of an actuator. The respective transceiver module 64 being connected to the EMG electrodes 60 and external sensor modules 50 via electrical pathways or wires (not shown). The transceiver module 64 being further being connected either wirelessly or via electrical pathways or wires (not shown) to a central database or database system (not shown), uses the subject's 70 movement data and a trained algorithm to correlate with the database to determine a preferred treatment protocol for the subject. The transceiver being still further connected to a controller (not shown), either wirelessly or via electrical pathways, uses the preferred treatment protocol to activate and deactivate an actuator (not shown) to release medication from the implantable reservoir 170.

Figure 12:
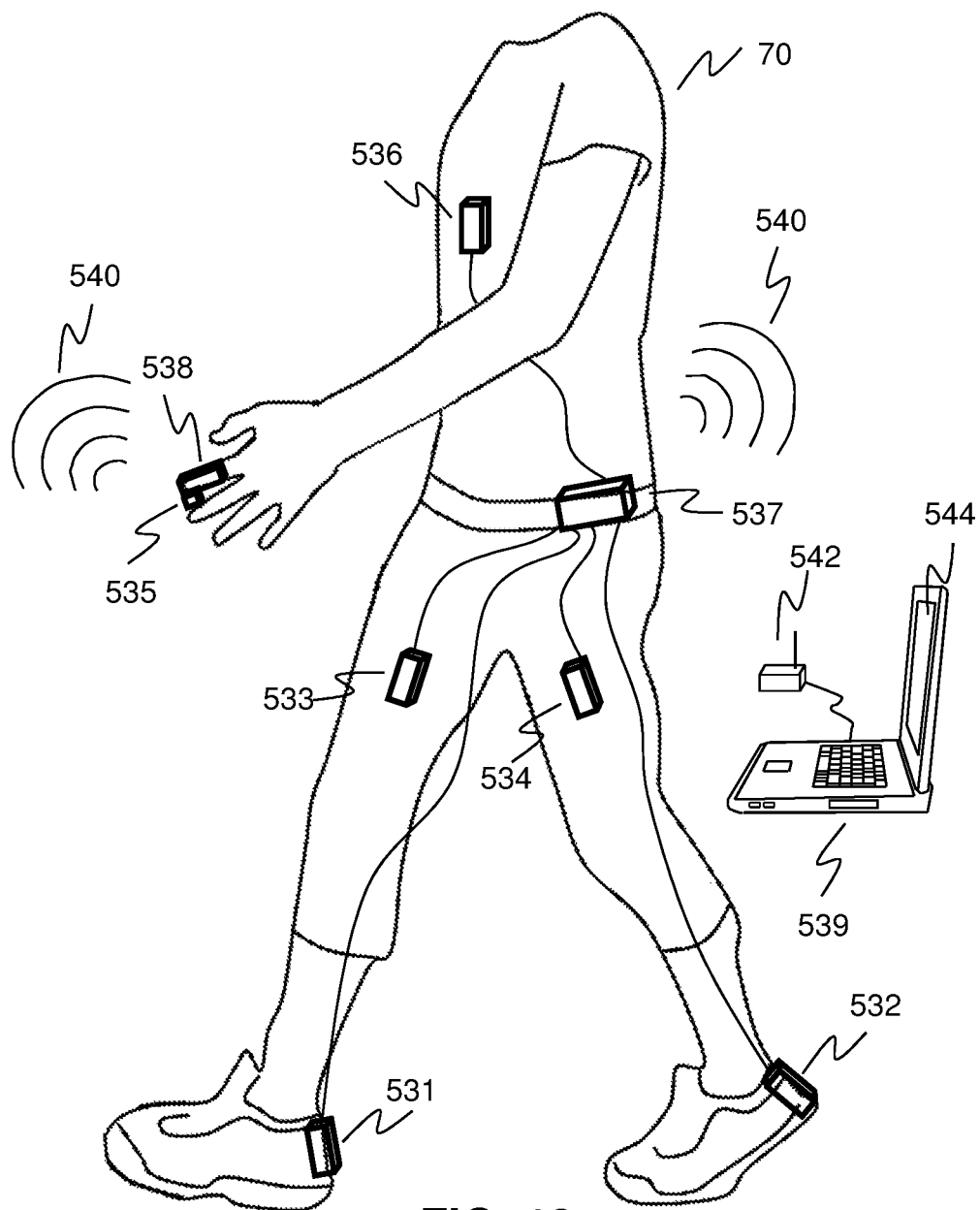
FIG. 12. Graphic depiction of a subject showing possible sensor units comprising accelerometers and gyroscopes in different embodiments of the present invention.

FIG. 12 illustrates possible sensor locations of a movement measuring device for different embodiments of the present invention. The subject 70 in this particular embodiment is wearing six sensor units 531-536 comprising accelerometers and gyroscopes (both not shown but described in more detail herein) for recording movement data. The subject 70 in this embodiment wears at least one sensor unit on a heel 531, 532, thigh 532, 534, finger 535, or torso 536. The subject 70 preferably may wear at least 2 sensor units on a combination of heels 531, 532, thighs 532, 534, fingers 535, or torso 536. Even more preferably, the subject 70 wears at least 4 sensor units on a combination of heels 531, 532, thighs 532, 534, fingers 535, or torso 536. Still even more preferably the subject 70 wears at least 8 sensor units on a combination of heels 531, 532, thighs 533, 534, fingers 535, joints (not shown), upper appendages (not shown), a waist (not shown), a torso 536, or other useful recording position known to someone skilled in the art. Additionally, a transceiver unit 537, 538 for preprocessing and transmitting the movement data may be wired or wireless with respect to both the sensors and an external processor 539. The movement data from the transceiver unit 537 or 538 is either stored transfer at a later time or for immediate transmission to a receiver unit 542 on the external processing unit via various mediums and transmission protocols, for example, radio link 540, or by Bluetooth, WIFI, or even USB (not shown), or the like. The processor (not shown) of the external processing unit 539 feeds the data into a trained algorithm preferably loaded into the processor implemented as firmware. The trained algorithm correlates with a central database (not shown) and outputs a patient customized treatment which may then be displayed on a monitor 544 or as input to control a treatment device (not shown) such as an electric stimulator, automated medicine delivery or titration device, or the like.

Figure 13:
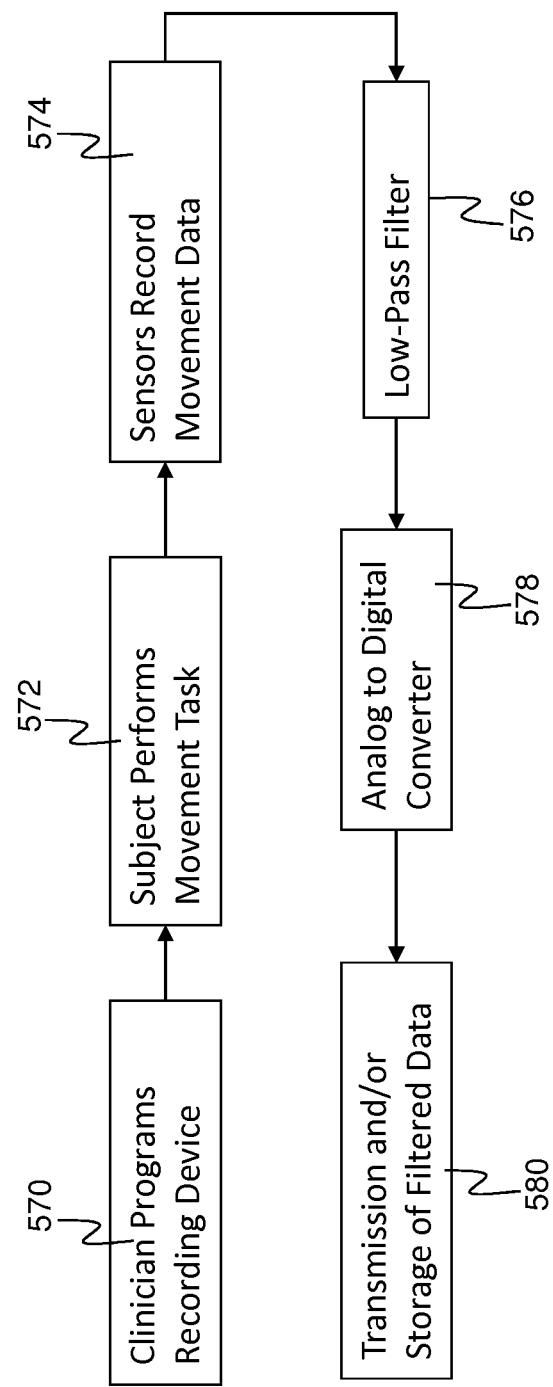
FIG. 13. Flow chart of preferable preprocessing steps.

FIG. 13 depicts preferable steps for preprocessing recorded movement data before extracting kinematic features or correlating it with a central database in order to determine a patient's treatment. Preferably this preprocessing is contained within the movement measuring apparatus, such as part of the transceiver unit, and consists of one or more electronic components. In various embodiments, a clinician first programs the recording device 570 to measure only at specific times or from specific sensors or even to measure continuously. Next, the subject performs movement tasks 572 according to the clinician's orders, either during specified tasks at the clinician's office, or at home during activities of daily living. While performing these tasks, the sensors of the movement measuring apparatus, preferably a combination of accelerometers and gyroscopes, record the subject's movement data 574. Once the movement data is recorded, preferably a low pass filter 576 is then used to remove all artifacts (including movement and electrical interference) or information known to those skilled in the art which would be unrelated to the subject's movement. Preferably the low pass filter allows only frequencies less than 100 Hz. Even more preferably, the low pass filter allows only frequencies less than 50 Hz. Even more preferably, the low pass filter allows only frequencies less than 30 Hz. Still more preferably, the low pass filter allows only frequencies less than 20 Hz. Next, an analog to digital converter (ADC) 578 may be used to digitize the data for future processing. Preferably, the ADC samples the recorded movement data at a rate of 120 Hz. Finally, the filtered data is either immediately transmitted or stored on board for later transmission 580 to a central database 504 or processor for use by a treatment customization algorithm.

Figure 14A:
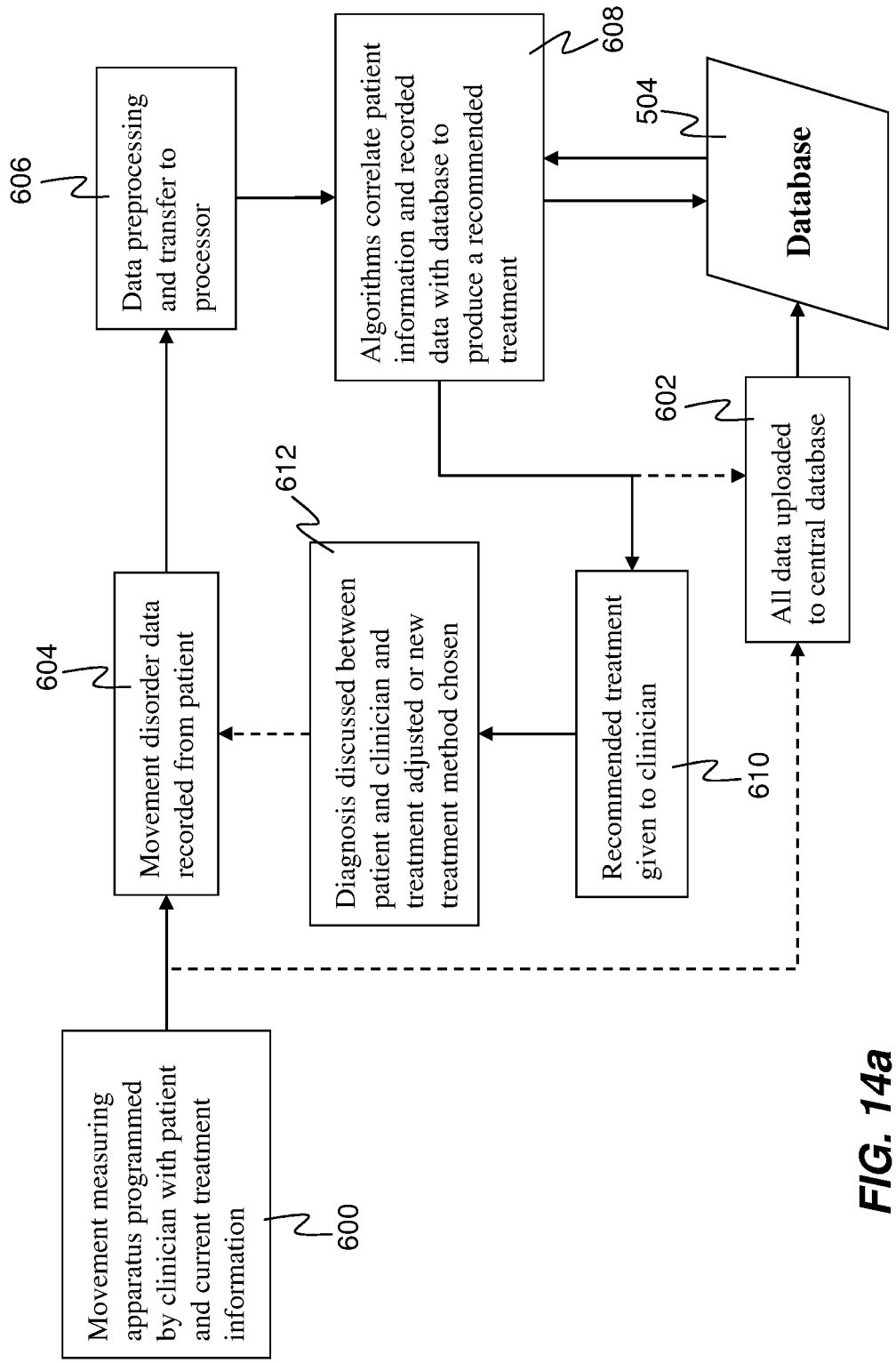
FIG. 14. Flow charts depicting the relational processes between a movement measuring apparatus, data, algorithms, clinician, patient, database, and treatment devices for a) report systems; and b) automated treatment systems.

FIG. 14 depicts the relational processes between a movement measuring apparatus, data, algorithms, clinician, patient, database, and treatment devices in many embodiments of the present invention. Like in FIG. 13, the first step in this process is the programming of the movement measuring apparatus by the clinician 600. In some embodiments, such recording will include the recording parameters, such as timing, and from which sensors, as well as information regarding the patient, such as their demographics, disorder and treatment history, and the like. Preferably, this data is immediately uploaded 602 to a central database 504 so as to create the most adaptable database possible for use in future treatment determinations. Next, as in FIG. 13, movement data is recorded from the patient 604, preferably from at least three-axes each of accelerometer and gyroscopic sensors. The data is then preprocessed and transferred 606 to a primary processor, as in one embodiment described in FIG. 13 by elements 576, 578, and 580. Next, a trained algorithm can be used 608 by a primary processor to correlate the recorded movement data 604 with a database 504. Preferably, there is two-way communication between the algorithm and database. The purpose of such communication is to look for which patient histories in the database are relevant, retrieve that information, and correlate the current patient information with the retrieved database information in order to produce a more customized and optimized treatment. Preferably, this treatment information is immediately uploaded 602 back to the central database 504 so as to create the most adaptable database possible for use in future treatment determinations. In FIG. 14a, a recommended treatment is then given 610 to a clinician, after which the treatment is either ordered and the patient's treatment device (an electrical stimulator, automated medication delivery device, or the like) re-programmed, or discussed with the patient 612. In FIG. 14b, after a treatment is determined, the treatment protocol is automatically programmed 614 in the treatment device (an electrical stimulator, automated medication delivery device, or the like).

Figure 15:
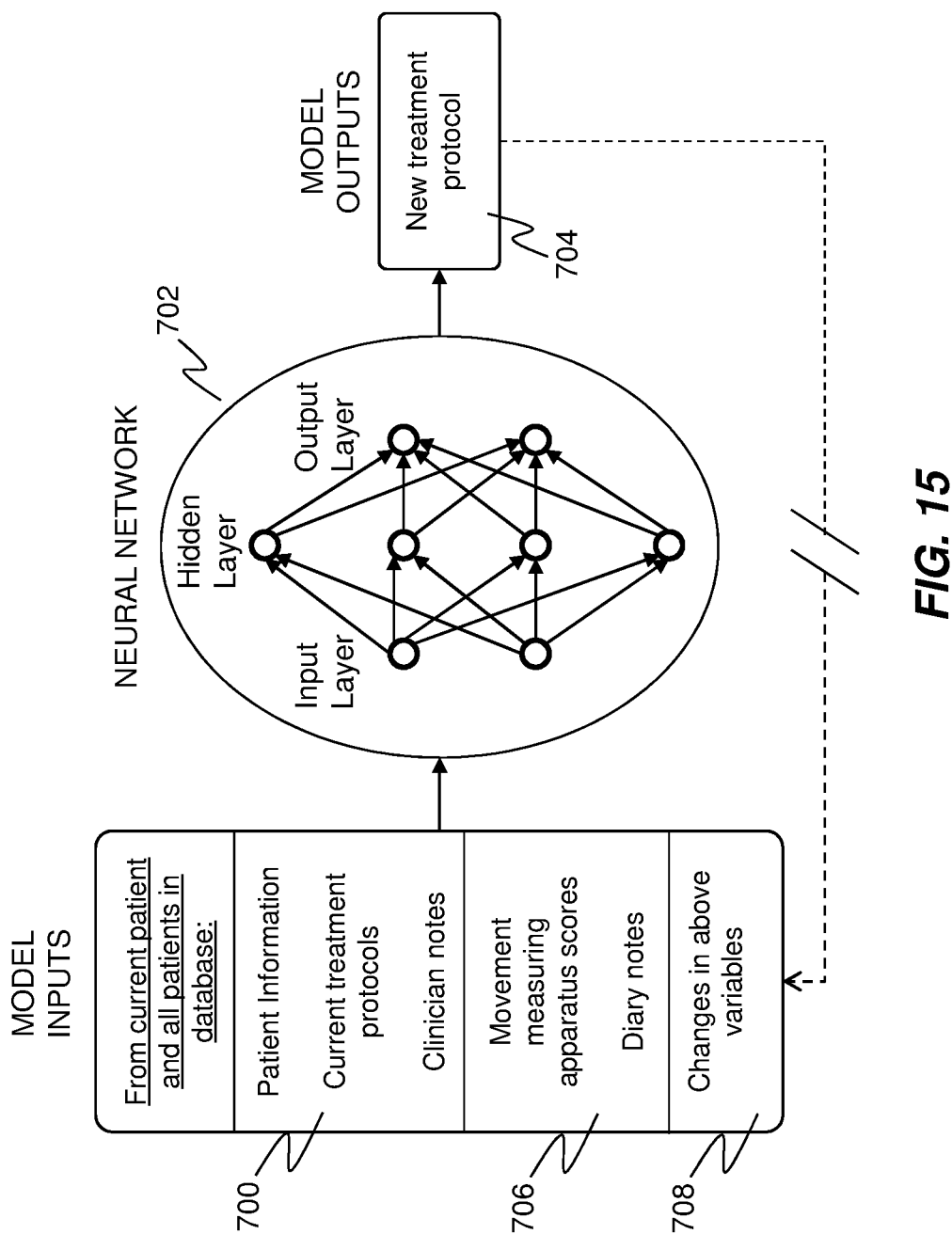
FIG. 15. Illustration of preferred multilayer perceptron artificial neural network model.

FIG. 15 is an illustration of the preferred embodiment of an artificial neural network algorithm used in correlating current patient data with a central database for determining a patient customized treatment protocol. The neural network itself 702 is preferably a feedforward model trained through back-propagation techniques and consisting of an input layer, hidden layer, and output layer. Preferably, there are multiple input layers, including but not limited to, clinical definitions 700 such as current patient demographics, disorder history, treatment history, clinician notes, and the like; subject data 706 such as recorded movement data, diary information, and the like; and a dynamic input 708 to account for changes in any of the other input variables with respect to time. The many inputs allow the algorithm to analyze complex data trends and dynamic interactions. Furthermore, multiple input layers allow constraints on the algorithm so that only the most appropriate data is used, while a dynamic layer helps optimize the correlation of that data to the subject's dynamic trends, so that the most efficient and optimized results are obtained. Still more preferably, data that is an input to the model is taken from or stored on a central database or database system of similar information for access by future subjects and algorithm training. The model output 704 is simply the new treatment protocol. While this new treatment protocol is not automatically fed back into the model input 700 as in a closed-loop iterative process, the information is preferably added to the central database so that it can be used in the future, thereby increasing the central database's adaptivity.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A system for providing treatment recommendations for movement disorders comprising:
   a movement measuring apparatus for measuring external body motion of a subject with a movement disorder and for calculating a movement score representative of a score that a skilled clinician might give to a subject during a movement analysis exam using a standardized scale, the movement measuring apparatus comprising at least one sensor and a transmitter;

an algorithm trained for correlating at least in part movement scores calculated from the subject with at least in part movement scores stored in at least one central database;

at least one central database where historical movement data comprising at least in part movement data, including at least in part movement scores, from a plurality of other subjects is stored;

a processor for correlating at least in part the calculated movement scores to the at least one central database and determining a recommended treatment using the algorithm; and a device for outputting or otherwise communicating the recommended treatment to a clinician or other user for review and administering;

wherein the at least one central database contains at least former patient disorder and treatment information; and the algorithm is trained through a supervised learning process that uses as algorithm inputs at least any three of patient demographics, treatment history, disorder details, recorded movement data, current treatment protocols, and movement scores, and uses as matched outputs recommended treatment stimulation parameters; and the algorithm performs a stepwise regression to determine a combination of algorithm inputs and matched outputs with a correlation to clinician treatments for subjects, wherein, when calculated by the processor or algorithm, the resultant correlation to clinician treatments for subjects with successful outcomes has a correlation coefficient of greater than 0.25.

2. The system of claim 1, wherein the at least one sensor is selected from the group consisting of accelerometers, gyroscopes, magnetometers, resistive bend sensors, and load cells.

3. The system of claim 2, wherein the algorithm is trained with a training set that only includes subject data where treatment was successful.

4. The system of claim 3, wherein the training set only includes subject data where movement scores based on measured external body motion decreased by more than 10%.

5. The system of claim 1, wherein the algorithm for correlating movement data is an artificial neural network in the form of a multilayer perceptron.

6. A method for providing treatment recommendations for movement disorders comprising steps of:
providing a movement measuring apparatus comprising at least one sensor and a transmitter, the movement measuring apparatus adapted to measure external body motion of a subject;
measuring external body motion of a subject wearing the movement measuring apparatus;
calculating at least one movement score representative of a score that a skilled clinician might give to a subject during a movement analysis exam using a standardized scale based at least in part on the measured external body motion of the subject;
transmitting the calculated at least one movement score from the movement measuring apparatus to a processor;
training an algorithm to correlate the at least one movement score with a database of movement data;
correlating with the processor the at least one movement score to at least one central database comprising movement data, including movement scores, from a plurality of other subjects using the algorithm, the database further comprising recommended treatment protocols; and
determining a recommended treatment based at least in part on the correlation between the at least one movement score and the at least one central database;
wherein the training of the algorithm is performed using a backpropagation technique on a feedforward model comprising at least three input layers, at least one hidden layer, and at least one output layer, and wherein the at least three input layers consist at least of:
clinical definitions, comprising one or more of current patient demographics, disorder history, treatment history, or clinician notes;
subject data, comprising one or more of recorded movement data and diary information; and
a dynamic input that accounts for changes in any other input variables with respect to time.

7. The method of claim 6, wherein the plurality of other subjects in the at least one central database suffer from similar movement disorders.

8. A method for providing treatment recommendations for movement disorders comprising steps of:
providing a movement measuring apparatus comprising at least one sensor and a transmitter, the movement measuring apparatus adapted to measure external body motion of a subject;
measuring external body motion of a subject wearing the movement measuring apparatus;
calculating at least one movement score representative of a score that a skilled clinician might give to a subject during a movement analysis exam using a standardized scale based at least in part on the measured external body motion of the subject;
transmitting the calculated at least one movement score from the movement measuring apparatus to a processor;
training an algorithm to correlate the at least one movement score with a database of movement data;
correlating with the processor the at least one movement score to at least one central database comprising movement data, including movement scores, from a plurality of other subjects using the algorithm, the database further comprising recommended treatment protocols; and
determining a recommended treatment based at least in part on the correlation between the at least one movement score and the at least one central database,
wherein the algorithm is a neural network algorithm, and the step of training the algorithm comprises using a set of input variables and neural network layer weights to test the neural network's ability to generalize data using a "one left out" technique where training data consists of all but one subject, a "left out" subject, and the training data is used to solve for the neural network weights, and the "left out" subject is then input to the neural network to generate predicted treatments.

9. The method of claim 8, wherein the training step is repeated for each subject in the training data, and success criteria of at least 80% agreement between the generated predicted treatments and the recommended treatment protocols is determined separately for at least two elements of an electric stimulation treatment protocol, the elements selected from the group consisting of contacts voltage, frequency, and pulse width.

10. A method for providing treatment recommendations for movement disorders comprising steps of:
providing a movement measuring apparatus comprising at least one sensor and a transmitter, the movement measuring apparatus adapted to measure external body motion of a subject;

measuring external body motion of a subject wearing the movement measuring apparatus;

calculating at least one movement score representative of a score that a skilled clinician might give to a subject during a movement analysis exam using a standardized scale based at least in part on the measured external body motion of the subject;

transmitting the calculated at least one movement score from the movement measuring apparatus to a processor;

training an algorithm to correlate the at least one movement score with a database of movement data;

correlating with the processor the at least one movement score to at least one central database comprising movement data, including movement scores, from a plurality of other subjects using the algorithm, the database further comprising recommended treatment protocols; and determining a recommended treatment based at least in part on the correlation between the at least one movement score and the at least one central database, wherein the at least one central database contains at least former patient disorder and treatment information; and the algorithm is trained through a supervised learning process that uses as algorithm inputs at least any three of patient demographics, treatment history, disorder details, recorded movement data, current treatment protocols, and movement scores, and uses as matched outputs recommended treatment stimulation parameters; and the combination of algorithm inputs and matched outputs is determined using a stepwise regression wherein the resultant correlation to clinician treatments for subjects with successful outcomes has a correlation coefficient of greater than 0.25.

* * * * *